US011580639B2

(12) United States Patent
Oh et al.

(10) Patent No.: US 11,580,639 B2
(45) Date of Patent: Feb. 14, 2023

(54) ELECTRONIC DEVICE FOR MEASURING SKIN CONDITION OF USER AND METHOD FOR OPERATING SAME

(71) Applicant: SAMSUNG ELECTRONICS CO., LTD., Suwon-si (KR)

(72) Inventors: Youngjae Oh, Suwon-si (KR); Yoonhee Choi, Suwon-si (KR); Jinhong Min, Suwon-si (KR); Hyoungseon Choi, Suwon-si (KR); Joonho Kim, Suwon-si (KR); Sangkyung Lee, Suwon-si (KR); Changwon Son, Suwon-si (KR); Younjoo Song, Suwon-si (KR); Seoyoung Yoon, Suwon-si (KR); Taehan Jeon, Suwon-si (KR); Hyunjoo Jung, Suwon-si (KR); Jiwoon Jung, Suwon-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 23 days.

(21) Appl. No.: 17/120,594

(22) Filed: Dec. 14, 2020

(65) Prior Publication Data

US 2021/0183058 A1 Jun. 17, 2021

(30) Foreign Application Priority Data

Dec. 13, 2019 (KR) .......................... 10-2019-0167027

(51) Int. Cl.
*G06T 7/00* (2017.01)
*G16H 30/20* (2018.01)
(Continued)

(52) U.S. Cl.
CPC .......... *G06T 7/0012* (2013.01); *A61B 5/0022* (2013.01); *A61B 5/0077* (2013.01);
(Continued)

(58) Field of Classification Search
CPC ......... G06T 7/0012; G06T 2207/10152; G06T 2207/30088; G06T 2207/30201;
(Continued)

(56) References Cited

U.S. PATENT DOCUMENTS 10,085,643 B2 * 10/2018 Bandic ................ A61B 5/4875
10,502,921 B1    12/2019 Wauchop
(Continued)

FOREIGN PATENT DOCUMENTS

CN          108143398        6/2018
JP          2005-182515      7/2005
(Continued)

OTHER PUBLICATIONS

International Search Report and Written Opinion dated Mar. 25, 2021 in corresponding International Application No. PCT/KR2020/018184.

*Primary Examiner* — Dramos Kalapodas
(74) *Attorney, Agent, or Firm* — Nixon & Vanderhye P.C.

(57) ABSTRACT

A first electronic device according to various embodiments may include: a display; a communication module comprising communication circuitry; a camera module including at least one camera; and a processor. The processor may be configured to: identify a request for measuring a skin condition of a user in a state in which the first electronic device is cradled on a second electronic device; acquire, based on information of the camera module and information regarding at least one light-emitting element included in the second electronic device, control information for controlling output of the at least one light-emitting element; control output of light from the at least one light-emitting element of the second electronic device based on the control information; acquire at least one image including at least a part of a body of the user through the camera module while light is output through the at least one light-emitting element
(Continued)

controlled based on the control information; and provide information regarding the skin condition of the user using the at least one image.

19 Claims, 15 Drawing Sheets

(51) Int. Cl.
*H04N 5/235* (2006.01)
*G16H 50/30* (2018.01)
*A61B 5/00* (2006.01)
*G06V 40/16* (2022.01)

(52) U.S. Cl.
CPC ............ *A61B 5/0079* (2013.01); *A61B 5/442* (2013.01); *G06V 40/171* (2022.01); *G16H 30/20* (2018.01); *G16H 50/30* (2018.01); *H04N 5/2352* (2013.01); *G06T 2207/10152* (2013.01); *G06T 2207/30088* (2013.01); *G06T 2207/30201* (2013.01)

(58) Field of Classification Search
CPC ... A61B 5/0022; A61B 5/0077; A61B 5/0079; A61B 5/442; A61B 2560/0456; A61B 5/441; A61B 5/6898; A61B 5/0013; A61B 5/0002; A61B 5/7465; G06V 40/171; G06V 10/141; G16H 30/20; G16H 50/30; G16H 30/40; G16H 50/20; G16H 40/67; H04N 5/2352; H04N 5/232
See application file for complete search history.

(56) References Cited

U.S. PATENT DOCUMENTS

| | | | |
|---|---|---|---|
| 2008/0105745 A1* | 5/2008 | Lei | G06K 7/10722 235/462.1 |
| 2008/0105746 A1* | 5/2008 | Lei | G06K 7/10851 235/462.11 |
| 2008/0105748 A1* | 5/2008 | Lei | G06K 7/10722 235/462.42 |
| 2008/0105749 A1* | 5/2008 | Lei | G06K 7/10722 235/462.42 |
| 2010/0185064 A1* | 7/2010 | Bandic | A61B 5/444 600/306 |
| 2011/0306859 A1* | 12/2011 | Saldivar | A61B 5/6823 607/9 |
| 2012/0321759 A1* | 12/2012 | Marinkovich | A61B 5/442 356/402 |
| 2014/0347512 A1 | 11/2014 | Sethi | |
| 2015/0355527 A1 | 12/2015 | Takahashi et al. | |
| 2017/0316564 A1 | 11/2017 | Igami et al. | |
| 2017/0340198 A1* | 11/2017 | Elazar | H04N 5/2253 |
| 2017/0340267 A1 | 11/2017 | Shen et al. | |
| 2018/0260871 A1* | 9/2018 | Harvill | G06F 16/9038 |
| 2021/0153752 A1* | 5/2021 | Park | A61B 5/746 |

FOREIGN PATENT DOCUMENTS

| | | |
|---|---|---|
| JP | 2012-151715 | 8/2012 |
| KR | 10-2015-0094751 | 8/2015 |
| KR | 10-1772218 | 8/2017 |
| KR | 10-2018-0061645 | 6/2018 |
| KR | 10-2018-0080140 | 7/2018 |
| KR | 10-2019-0074479 | 6/2019 |
| KR | 10-2019-0136599 | 12/2019 |

* cited by examiner

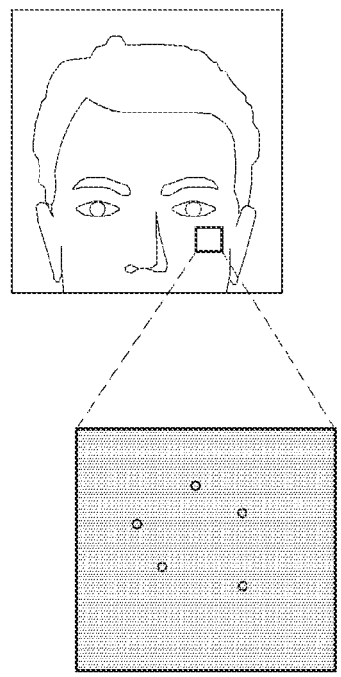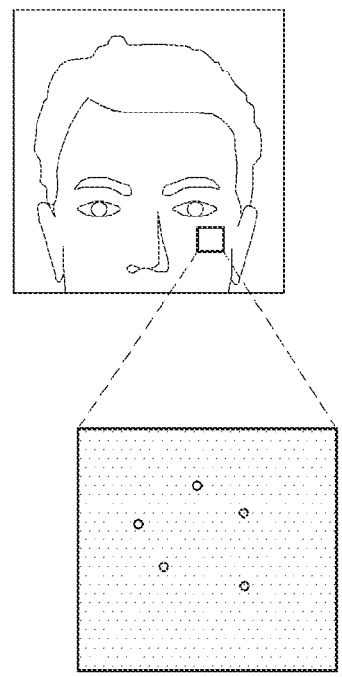
FIG.14A     FIG.14B
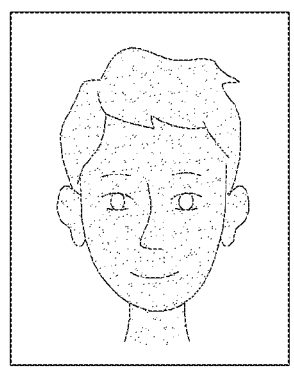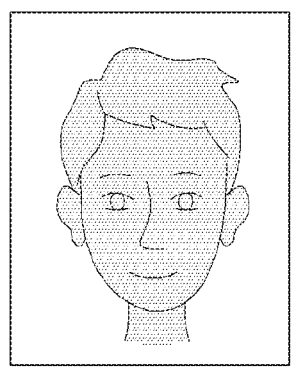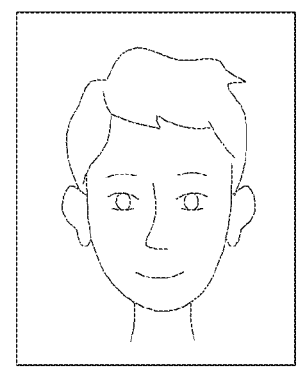
FIG.15A     FIG.15B     FIG.15C

ELECTRONIC DEVICE FOR MEASURING SKIN CONDITION OF USER AND METHOD FOR OPERATING SAME

CROSS-REFERENCE TO RELATED APPLICATION

This application is based on and claims priority under 35 U.S.C. § 119 to Korean Patent Application No. 10-2019-0167027, filed on Dec. 13, 2019, in the Korean Intellectual Property Office, the disclosure of which is incorporated by reference herein in its entirety.

BACKGROUND

Field

The disclosure relates to an electronic device for measuring the skin condition of a user and a method for operating the same.

Description of Related Art

There has recently been widespread use of various kinds of electronic devices, such as a smartphone, a tablet PC, a portable multimedia player (PMP), a personal digital assistant (PDA), a laptop PC, and a wearable device. In addition, various types of smart home appliances have also been widely used.

Various services and additional functions provided by electronic devices, for example, portable electronic devices such as smartphones, have been increasing gradually. In order to improve the usability of such electronic devices and to satisfy various user demands, electronic device manufacturers tend to provide various functions interlinked with other home appliances. Accordingly, highly diversified functions are provided by electronic devices.

In connection with an electronic device for analyzing the user's skin condition, accurate analysis of the skin condition requires an appropriate level of lighting. If the level of brightness of the lighting necessary to analyze the skin condition is too high or too low, the user's skin condition may fail to be analyzed accurately. For example, if the brightness of external lighting positioned near the user, whose skin condition is to be measured, cannot be adjusted, there may be a difficulty in measuring the accurate skin condition. That is, the output of the external light needs to be controlled to measure the accurate skin condition. In addition, light customized to the user's skin condition to be measured (for example, pigmentation, small wrinkles, or the like) is necessary, and the output of the external lighting should therefore be controlled according to the user's skin condition to be measured.

SUMMARY

Embodiments of the disclosure provide an electronic device capable of controlling the output of a light-emitting module of an external electronic device when measuring the user's skin condition, and a method for operating the same.

A first electronic device according to various example embodiments may include: a display; a communication module comprising communication circuitry; a camera module including a camera; and a processor. The processor may be configured to: identify a request for measuring a skin condition of a user in a state in which the first electronic device is cradled on a second electronic device; acquire, based on information of the camera module and information regarding at least one light-emitting element included in the second electronic device, control information for controlling output of the at least one light-emitting element; control output of light from the at least one light-emitting element of the second electronic device based on the control information; acquire at least one image including at least a part of a body of the user through the camera module while light is output through the at least one light-emitting element controlled by the control information; and provide information regarding the skin condition of the user using the at least one image.

A method for operating a first electronic device according to various example embodiments may include: identifying a request for measuring a skin condition of a user in a state in which the first electronic device is cradled on a second electronic device; acquiring, based on information of a camera included in the first electronic device and information regarding at least one light-emitting element included in the second electronic device, control information for controlling output of light from the at least one light-emitting element; controlling output of light from the at least one light-emitting element of the second electronic device based on the control information; acquiring at least one image including at least a part of a body of the user through the camera while light is output through the at least one light-emitting element controlled by the control information; and providing information regarding the skin condition of the user using the at least one image.

An electronic device according to various example embodiments may include: at least one light-emitting element; and a processor. The processor may be configured to: control the at least one light-emitting element to enter a standby state based on an external electronic device being cradled on the electronic device; control the at least one light-emitting element to output light based on control information acquired from the external electronic device, the control information being determined based on information of a camera module of the external electronic device and information regarding the at least one light-emitting element; and stop output of light from the at least one light-emitting element based on image capturing by the external electronic device being completed.

According to various embodiments, a method may be advantageously provided, wherein, when measuring the user's skin condition, an electronic device can control the output of a light-emitting module of an external electronic device, thereby measuring the user's skin condition more accurately.

BRIEF DESCRIPTION OF THE DRAWINGS

The above and other aspects, features, and advantages of certain embodiments of the present disclosure will be more apparent from the following detailed description, taken in conjunction with the accompanying drawings, in which:

FIG. 14A is a diagram illustrating an example result of measuring the user's skin according to the brightness of light output from a light-emitting module of a second electronic device according to various embodiments;

FIG. 14B is a diagram illustrating an example result of measuring the user's skin according to the brightness of light output from a light-emitting module of a second electronic device according to various embodiments;

FIG. 15A is a diagram illustrating an example result of measuring the user's skin using a polarizing filter of a second electronic device according to various embodiments;

FIG. 15B is a diagram illustrating an example result of measuring the user's skin using a polarizing filter of a second electronic device according to various embodiments; and FIG. 15C is a diagram illustrating an example result of measuring the user's skin using a polarizing filter of a second electronic device according to various embodiments.

DETAILED DESCRIPTION

Figure 1:
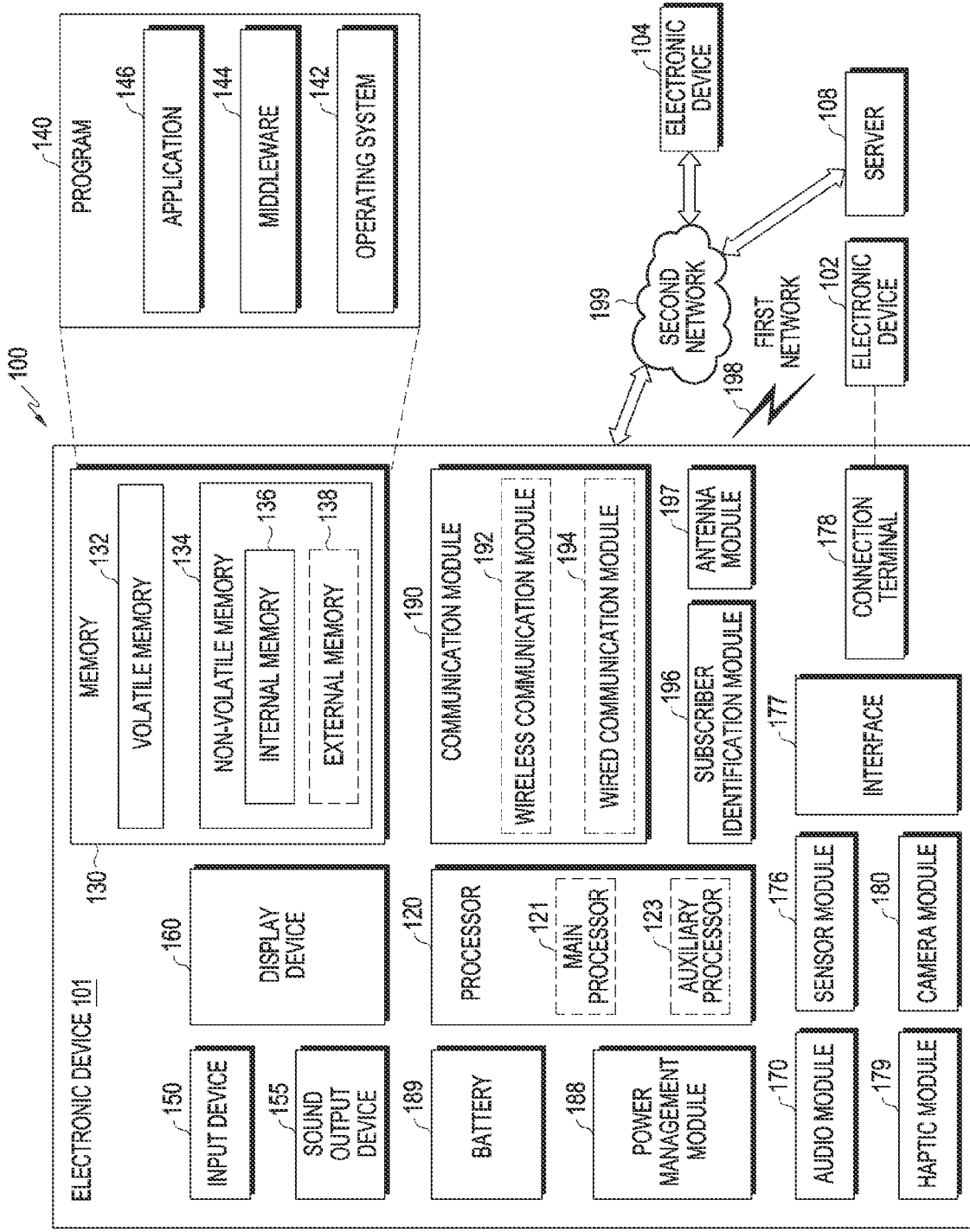
FIG. 1 is a block diagram illustrating an example electronic device in a network environment according to various embodiments.

FIG. 1 is a block diagram illustrating an example electronic device 101 in a network environment 100 according to various embodiments. Referring to FIG. 1, the electronic device 101 in the network environment 100 may communicate with an electronic device 102 via a first network 198 (for example, a short-range wireless communication network), or may communicate with an electronic device 104 or a server 108 via a second network 199 (for example, a long-range wireless communication network). According to an embodiment, the electronic device 101 may communicate with the electronic device 104 via the server 108. According to an embodiment, the electronic device 101 may include a processor 120, memory 130, an input device 150, a sound output device 155, a display device 160, an audio module 170, a sensor module 176, an interface 177, a haptic module 179, a camera module 180, a power management module 188, a battery 189, a communication module 190, a subscriber identification module 196, or an antenna module 197. In some embodiments, at least one (for example, the haptic module 179 or the subscriber identification module 196) of the components of the electronic device 101 may be omitted, or one or more other components may be added thereto. In some embodiments, some of the components may be implemented as single integrated circuitry. For example, the sensor module 176 (for example, a fingerprint sensor, an iris sensor, or an illuminance sensor) may be implemented to be embedded in the display device 160 (for example, a display).

The processor 120 may execute, for example, software (for example, a program 140) so as to control at least one other component (for example, a hardware or software component) of the electronic device 101 connected to the processor 120, and may perform various kinds of data processing or computation. According to an example embodiment, as at least part of the data processing or computation, the processor 120 may load a command or data received from another component (for example, the sensor module 176 or the communication module 190) into a volatile memory 132, may process the command or data stored in the volatile memory 132, and may store resulting data in a nonvolatile memory 134. According to an embodiment, the processor 120 may include a main processor 121 (for example, a central processing device or an application processor (AP)), and an auxiliary processor 123 (for example, a graphic processing device, an image signal processor, a sensor hub processor, or a communication processor) that is operable independently from or in conjunction with the main processor 121. Additionally or alternatively, the auxiliary processor 123 may be configured to consume less power than the main processor 121 or to be specified to a designated function. The auxiliary processor 123 may be implemented separately from, or as a part of the main processor 121.

The auxiliary processor 123 may control at least some of functions or states related to at least one component (for example, the display device 160, the sensor module 176, or the communication module 190) among the components of the electronic device 101, instead of the main processor 121 while the main processor 121 is in an inactive (for example, sleep) state, or together with the main processor 121 while the main processor 121 is in an active state (for example, executing an application). According to an embodiment, the auxiliary processor 123 (for example, an image signal processor or a communication processor) may be implemented as a part of another component (for example, the camera module 180 or the communication module 190) functionally related thereto.

The memory 130 may store various kinds of data used by at least one component (for example, the processor 120 or the sensor module 176) of the electronic device 101. The data may include, for example, software (for example, the program 140) and input data or output data regarding a command related thereto. The memory 130 may include a volatile memory 132 or a nonvolatile memory 134.

The program 140 may be stored in the memory 130 as software, and may include, for example, an operating system 142, middleware 144, or an application 146.

The input device 150 may receive a command or data to be used by other components (for example, the processor 120) of the electronic device 101, from the outside (for example, a user) of the electronic device 101. The input device 150 may include, for example, a microphone, a mouse, or a keyboard, or a digital pen (for example, a stylus pen).

The sound output device 155 may output sound signals to the outside of the electronic device 101. The sound output device 155 may include, for example, a speaker or a receiver. The speaker may be used for general purposes, such as playing multimedia files or playing recorded sounds, and the receiver may be used to receive incoming calls. According to an embodiment, the receiver may be implemented separately from, or as a part of the speaker.

The display device 160 may visually provide information to the outside (for example, a user) of the electronic device 101. The display device 160 may include, for example, a display, a hologram device, or a projector and control circuitry to control the corresponding device. According to an embodiment, the display device 160 may include touch circuitry configured to detect a touch, or sensor circuitry (for example, a pressure sensor) configured to measure the intensity of the force incurred by the touch.

The audio module 170 may convert a sound into an electrical signal or vice versa. According to an embodiment, the audio module 170 may obtain the sound via the input device 150, or output the sound via the sound output device 155 or an external electronic device (for example, an electronic device 102) (for example, a speaker or a headphone) directly or wirelessly connected to the electronic device 101.

The sensor module 176 may sense an operational state (for example, power or temperature) of the electronic device 101 or an environmental state (for example, a user state) external to the electronic device 101, and may produce an electrical signal or a data value corresponding to the sensed state. According to an embodiment, the sensor module 176 may include, for example, a gesture sensor, a gyro sensor, an atmospheric pressure sensor, a magnetic sensor, an acceleration sensor, a grip sensor, a proximity sensor, a color sensor, an infrared (IR) sensor, a biometric sensor, a temperature sensor, a humidity sensor, or an illuminance sensor.

The interface 177 may support one or more specified protocols that can be used by the electronic device 101 to be connected to the external electronic device (for example, the electronic device 102) directly or wirelessly. According to an embodiment, the interface 177 may include, for example, a high definition multimedia interface (HDMI), a universal serial bus (USB) interface, ad (SD card interface, or an audio interface.

The connecting terminal 178 may include a connector via which the electronic device 101 may be physically connected to the external electronic device (for example, the electronic device 102). According to an embodiment, the connecting terminal 178 may include, for example, an HDMI connector, a USB connector, an SD card connector, or an audio connector (for example, a headphone connector).

The haptic module 179 may convert an electrical signal into a mechanical stimulus (for example, a vibration or a movement) or an electrical stimulus, which may be recognized by the user via his/her tactile sensation or kinesthetic sense. According to an embodiment, the haptic module 179 may include, for example, a motor, a piezoelectric element, or an electric stimulus device.

The camera module 180 may capture still images and moving images. According to an embodiment, the camera module 180 may include one or more lenses, image sensors, image signal processors, or flashes.

The power management module 188 may manage power supplied to the electronic device 101. According to an example embodiment, the power management module 188 may be implemented as at least part of, for example, a power management integrated circuit (PMIC).

The battery 189 may supply power to at least one component of the electronic device 101. According to an embodiment, the battery 189 may include, for example, a primary cell which is not rechargeable, a secondary cell which is rechargeable, or a fuel cell.

The communication module 190 may establish a direct (for example, wired) communication channel or a wireless communication channel between the electronic device 101 and the external electronic device (for example, the electronic device 102, the electronic device 104, or the server 108) and may support communication performed via the established communication channel. The communication module 190 may include one or more communication processors which are run independently of the processor 120 (for example, the application processor), and which support direct (for example, wired) communication or wireless communication. According to an embodiment, the communication module 190 may include a wireless communication module 192 (for example, a cellular communication module, a short-range wireless communication module, or a global navigation satellite system (GNSS) communication module) or a wired communication module 194 (for example, a local area network (LAN) communication module or a power line communication module). A corresponding one of these communication modules may communicate with the external electronic device via the first network 198 (for example, a short-range communication network such as Bluetooth, Wi-Fi direct, or infrared data association (IrDA)) or the second network 199 (for example, a long-range communication network such as a cellular network, the Internet, or a computer network (for example, LAN or WAN). These various types of communication modules may be implemented as a single component (for example, a single chip), or may be implemented as multiple components (for example, multiple chips) separate from each other. The wireless communication module 192 may identify and authenticate the electronic device 101 in a communication network, such as the first network 198 or the second network 199, using subscriber information (for example, international mobile subscriber identity (IMSI)) stored in the subscriber identification module 196.

The antenna module 197 may transmit or receive a signal or power to or from the outside (for example, the external electronic device). According to an embodiment, the antenna module may include an antenna including a radiating element made of a conductive material or a conductive pattern formed on a substrate (for example, a PCB). According to an embodiment, the antenna module 197 may include multiple antennas. In such a case, at least one antenna appropriate for a communication scheme used in the communication network, such as the first network 198 or the second network 199, may be selected, for example, by the communication module 190 from the multiple antennas. The signal or power may then be transmitted or received between the communication module 190 and the external electronic device via the selected at least one antenna. According to an embodiment, another component (for example, an RFIC) other than the radiating element may be additionally formed as a part of the antenna module 197.

At least some of the above-described components may be connected to each other so as to exchange signals (for example, commands or data) therebetween via an inter-peripheral communication scheme (for example, a bus, a general purpose input and output (GPIO), a serial peripheral interface (SPI), or a mobile industry processor interface (MIPI)).

According to an embodiment, commands or data may be transmitted or received between the electronic device 101 and the external electronic device 104 via the server 108 connected to the second network 199. Each of the electronic devices 102 and 104 may be a device of the same type as, or a different type from the electronic device 101. According to an embodiment, all or some of operations executed by the electronic device 101 may be executed by one or more of the external electronic devices 102, 104, or 108. For example, if the electronic device 101 needs to perform a function or a service automatically, or in response to a request from the user or another device, the electronic device 101 may request one or more external electronic devices to perform at least a part of the function or the service, instead of or in addition to executing the function or the service independently. Upon receiving the request, one or more external electronic devices may execute at least a part of the function or the service requested, or an additional function or an additional service related to the request, and may deliver the result of execution to the electronic device 101. The electronic device 101 may provide the result, with or without further processing the same, as at least a part of a reply to the request. To this end, a cloud computing, distributed computing, or client-server computing technology may be used, for example.

The electronic device according to various embodiments may be one of various types of electronic devices. The electronic devices may include, for example, and without limitation, a portable communication device (e.g., a smart phone), a computer device, a portable multimedia device, a portable medical device, a camera, a wearable device, a home appliance, or the like. The electronic device according to embodiments of the disclosure is not limited to those described above.

It should be appreciated that various embodiments of the disclosure and the terms used therein are not intended to limit the technological features set forth herein to particular embodiments and include various changes, equivalents, or alternatives for a corresponding embodiment. With regard to the description of the drawings, similar reference numerals may be used to designate similar or relevant elements. It is to be understood that a singular form of a noun corresponding to an item may include one or more of the things, unless the relevant context clearly indicates otherwise. As used herein, each of such phrases as "A or B," "at least one of A and B," "at least one of A or B," "A, B, or C," "at least one of A, B, and C," and "at least one of A, B, or C," may include all possible combinations of the items enumerated together in a corresponding one of the phrases. As used herein, such terms as "a first", "a second", "the first", and "the second" may be used to simply distinguish a corresponding element from another, and does not limit the elements in other aspect (e.g., importance or order). It is to be understood that if an element (e.g., a first element) is referred to, with or without the term "operatively" or "communicatively", as "coupled with," "coupled to," "connected with," or "connected to" another element (e.g., a second element), the element may be coupled with the other element directly (e.g., wiredly), wirelessly, or via another element (e.g., third element).

As used herein, the term "module" may include a unit implemented in hardware, software, or firmware, or any combination thereof, and may be interchangeably used with other terms, for example, "logic," "logic block," "component," or "circuit". The "module" may be a minimum unit of a single integrated component adapted to perform one or more functions, or a part thereof. For example, according to an embodiment, the "module" may be implemented in the form of an application-specific integrated circuit (ASIC).

Various embodiments as set forth herein may be implemented as software (e.g., the program 140) including one or more instructions that are stored in a storage medium (e.g., internal memory 136 or external memory 138) that is readable by a machine (e.g., the electronic device 101). For example, a processor (e.g., the processor 120) of the machine (e.g., the electronic device 101) may invoke at least one of the one or more instructions stored in the storage medium, and execute it, with or without using one or more other components under the control of the processor. This allows the machine to be operated to perform at least one function according to the at least one instruction invoked. The one or more instructions may include a code made by a complier or a code executable by an interpreter. The machine-readable storage medium may be provided in the form of a non-transitory storage medium. Wherein, the "non-transitory" storage medium is a tangible device, and may not include a signal (e.g., an electromagnetic wave), but this term does not differentiate between where data is semi-permanently stored in the storage medium and where the data is temporarily stored in the storage medium.

According to an embodiment, a method according to various embodiments of the disclosure may be included and provided in a computer program product. The computer program product may be traded as a product between a seller and a buyer. The computer program product may be distributed in the form of a machine-readable storage medium (e.g., compact disc read only memory (CD-ROM)), or be distributed (e.g., downloaded or uploaded) online via an application store (e.g., Play Store™), or between two user devices (e.g., smart phones) directly. If distributed online, at least part of the computer program product may be temporarily generated or at least temporarily stored in the machine-readable storage medium, such as memory of the manufacturer's server, a server of the application store, or a relay server.

According to various embodiments, each element (e.g., a module or a program) of the above-described elements may include a single entity or multiple entities. According to various embodiments, one or more of the above-described elements may be omitted, or one or more other elements may be added. Alternatively or additionally, a plurality of elements (e.g., modules or programs) may be integrated into a single element. In such a case, according to various embodiments, the integrated element may still perform one or more functions of each of the plurality of elements in the same or similar manner as they are performed by a corresponding one of the plurality of elements before the integration. According to various embodiments, operations performed by the module, the program, or another element may be carried out sequentially, in parallel, repeatedly, or heuristically, or one or more of the operations may be executed in a different order or omitted, or one or more other operations may be added.

Figure 2:
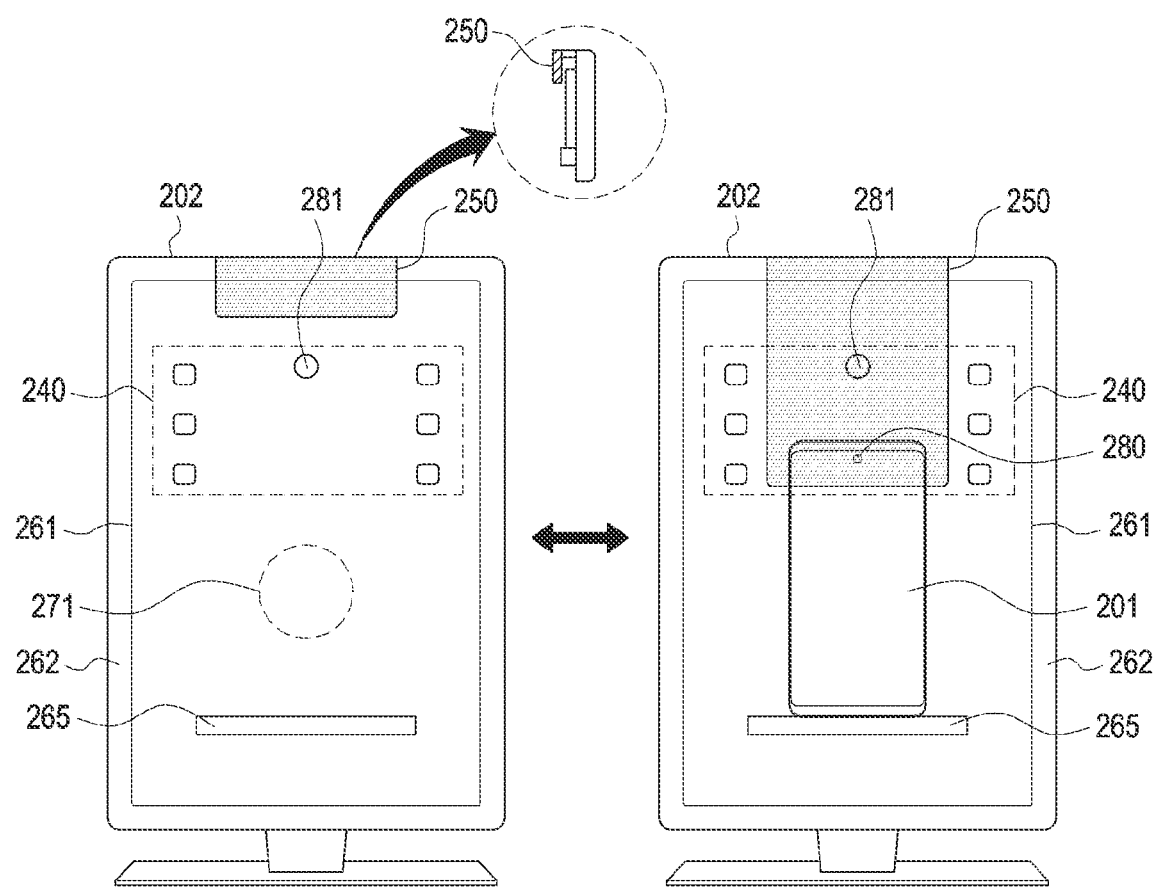
FIG. 2 is a diagram illustrating an example of a first electronic device and a second electronic device according to various embodiments.

FIG. 2 is a diagram illustrating an example of a first electronic device and a second electronic device according to various embodiments.

Referring to FIG. 2, the first electronic device 201 and the second electronic device 202 may be implemented identically or similarly to the electronic device 101 in FIG. 1. For example, the first electronic device 201 may be implemented as a smartphone or a tablet PC. The second electronic device 202 may be implemented as a smart mirror. For example, the smart mirror may refer to a device which includes a mirror, which can be connected to a network, which has an independent computing ability, and which can perform various functions through an application program or an application.

According to various embodiments, the first electronic device 201 may be cradled on the second electronic device 202. For example, the first electronic device 201 may be cradled on a cradle 265 of the second electronic device 202. For example, the cradle 265 may have a form illustrated in FIG. 2, which is only an example, and the form or shape of the cradle 265 may be variously modified. In addition, the cradle 265 may be positioned on a support rack on the lower end of the second electronic device 202. The cradle 265 may then be positioned outside the surface of the mirror 261. The cradle 265 may be replaced with an object including a magnetic material, to which the first electronic device 201 may be attached, for example. The object including a magnetic material may then be positioned inside the mirror 261. That is, if the cradle 265 is replaced with an object including a magnetic material, there may be no need for an object (for example, the cradle 265) for cradling the first electronic device 201 on the outside of the mirror 261.

According to various embodiments, when the first electronic device 201 is cradled on the second electronic device 202, the camera module 280 of the first electronic device 201 may capture an image. The first electronic device 201 may analyze the captured image, thereby providing information regarding the user's skin condition.

The position and/or number of the camera module 280 disposed on the front portion of the first electronic device 201, illustrated in FIG. 2, may not be limited. In addition, although it is assumed in the description with reference to FIG. 2 that the camera module 280 disposed on the front portion of the first electronic device 201 may be used to capture an image, the disclosure is not limited thereto. For example, a camera module disposed in the rear portion of the first electronic device 201 may be used to capture an image.

According to various embodiments, when the first electronic device 201 is cradled on the second electronic device 202, the first electronic device 201 may receive power from the second electronic device in a wired or wireless manner. The first electronic device 201 may transmit power to the second electronic device in a wired or wireless manner.

According to various embodiments, the second electronic device 202 may include a light-emitting module (e.g., including light-emitting elements and/or light-emitting circuitry) 240, an optical filter 250, a mirror 261, a lighting element 262, a cradle 265, a wireless charging module (e.g., including wireless charging circuitry) 271, and a camera module (e.g., including a camera) 281.

According to various embodiments, the light-emitting module 240 may include various light-emitting elements and/or light-emitting circuitry and output light for measuring the user's skin condition. The light-emitting module 240 may include multiple light-emitting elements. The multiple light-emitting elements may be positioned inside the mirror 261. When outputting no light, the multiple light-emitting elements may not be exposed to the outside. The multiple light-emitting elements may be positioned outside the mirror 261. The light-emitting module 240 may output light having a relatively high level of illuminance.

According to various embodiments, the light-emitting module 240 may include light-emitting elements outputting the same kind of light or different kinds of light. For example, the multiple light-emitting elements may output at least one of polarized light, ultraviolet rays, white light (for example, unpolarized white light), near-infrared rays, and infrared rays. In addition, for example, the multiple light-emitting elements may successively output at least one of polarized light, ultraviolet rays, white light, near-infrared rays, and infrared rays according to image capturing.

The multiple light-emitting elements included in the light-emitting module 240 illustrated in FIG. 2 are for convenience of description, and the number, size, position, and form of the elements may not be limited thereto. For example, the light-emitting module 240 may include a single light-emitting element.

According to various embodiments, the optical filter 250 may suppress light at the skin surface during skin imaging (for example, cross polarization), may inversely highlight the same (for example, parallel polarization), or may highlight a specific wavelength band (for example, a specific color). For example, the optical filter 250 may remove or highlight surface-reflected light. For example, the optical filter 250 may cause externally incident light to vibrate only in one direction, thereby allowing waves of the light to pass in one direction. For example, the optical filter 250 may be positioned above the camera 280 when the first electronic device 201 is cradled. That is, the optical filter 250 may filter light incident onto the camera 280 of the first electronic device 201. In addition, the optical filter 250 may be positioned above at least one of the multiple light-emitting elements. That is, the optical filter 250 may filter light output from at least one of the multiple light-emitting elements.

According to various embodiments, the optical filter 250 may include a specific wavelength band pass filter or a polarizing filter (or a polarizing film). For example, the specific wavelength band pass filter may refer to a filter configured to influence a wavelength component by transmitting red light only, among RGB colors of light, or by blocking ultraviolet rays. In addition, the polarizing filter may refer to a filter configured to determine whether or not light is transmitted, according to the direction of vibration of the light. For example, the optical filter 250 may be implemented in an attachable/detachable manner or in a foldable type. For example, when the optical filter 250 is implemented in an attachable/detachable manner, the optical filter 250 may be attached to/detached from the second electronic device 202.

The optical filter 250 illustrated in FIG. 2 is for convenience of description, and the number, size, position, and form of the optical filter 250 may not be limited thereto.

According to various embodiments, the mirror 261 may be exposed to the outside of the second electronic device 202. The mirror 261 may perform a display function. For example, the mirror 261 may include a half mirror. For example, the second electronic device 202 may be implemented such that the exterior thereof is covered by the half mirror, and a display is superimposed on the rear surface of the half mirror. For example, the mirror 261 may display information of the second electronic device 202 through the display and the half mirror. In addition, if the light-emitting module 240 is positioned inside the mirror 261, the light-emitting module 240 may transmit light through the half mirror, thereby outputting light to the outside. The light-emitting module 240 may output light to the outside through a transparent surface of the half mirror, from which metal coatings are selectively removed (or excluded).

According to various embodiments, the lighting element 262 may output light. For example, the lighting element 262 may be positioned in an edge area of the second electronic device 202. For example, the lighting element 262 may output light for a different purpose from the light-emitting module 240. For example, the lighting element 262 may output light (for example, white light) for a general purpose (for example, used by the user to put on makeup or to view a face), not for the purpose of measuring the user's skin. For example, the lighting element 262 may output light at a relatively low level of illuminance compared with the light-emitting module 240.

According to various embodiments, the cradle 265 may be used to cradle the first electronic device 201. For example, the height and/or leftward/rightward length of the cradle 265 may be adjusted. The cradle 265 may be attached to/detached from the second electronic device 202 using a magnet (or magnetic material). In addition, the height and/or leftward/rightward length of the cradle 265 may be adjusted in a sliding type.

The wireless charging module 271 may include various wireless charging circuitry and wirelessly transmit power to an external electronic device (for example, first electronic device 201). For example, if the first electronic device 201 is cradled on the cradle 265, the wireless charging module 271 may transmit power to the first electronic device 201. For example, the wireless charging module 271 may transmit power in a magnetic resonance type and/or a magnetic induction type. In addition, the wireless charging module 271 may receive power from the external electronic device (for example, first electronic device 201). The wireless charging module 271 may be positioned inside the second electronic device 202.

According to various embodiments, the second electronic device 202 may transmit power to the first electronic device 201 in a wired manner. For example, when connected to the first electronic device 201 by a wire (for example, USB wire), the second electronic device 202 may transmit power through the wire.

According to various embodiments, the camera module 281 may include at least one camera and capture images. For example, the camera module 281 may be positioned in an area which is not covered by the first electronic device 201, even if the first electronic device 201 is cradled. Images captured by the camera module 281 may be stored in the second electronic device 202 or transmitted to another electronic device (for example, first electronic device 201). Alternatively, images captured by the camera module 281 may be used by the second electronic device 202 to independently measure the user's skin condition.

The camera module 281 illustrated in FIG. 2 is for convenience of description, and the number, size, position, and form of the camera module 281 may not be limited thereto.

Figure 3A:
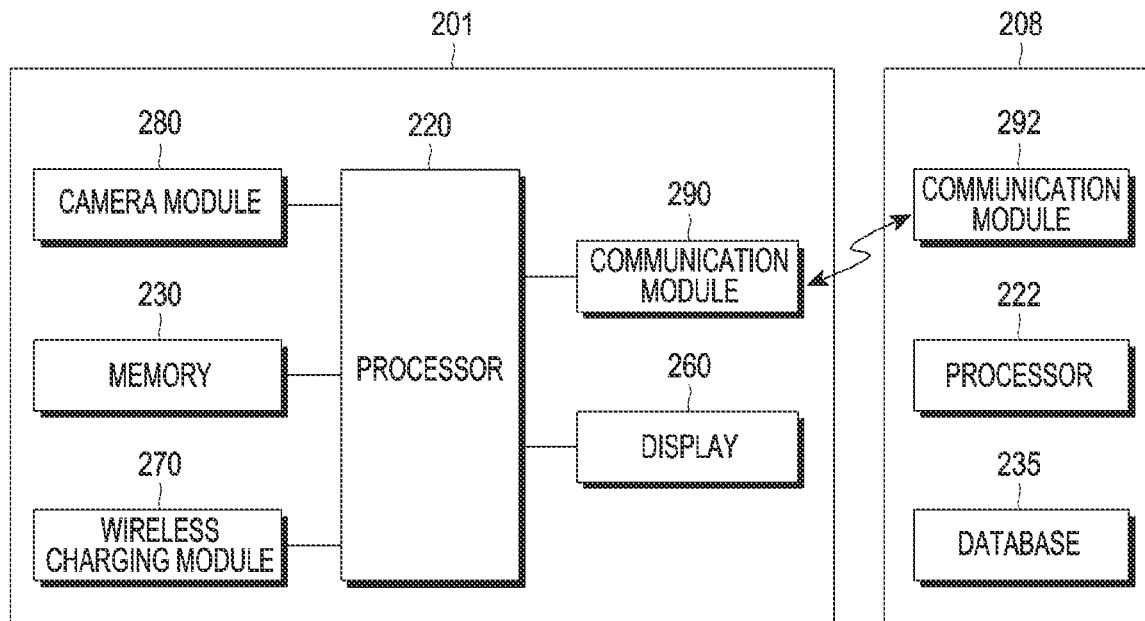
FIG. 3A is a block diagram illustrating an example first electronic device and a server according to various embodiments.
Figure 3B:
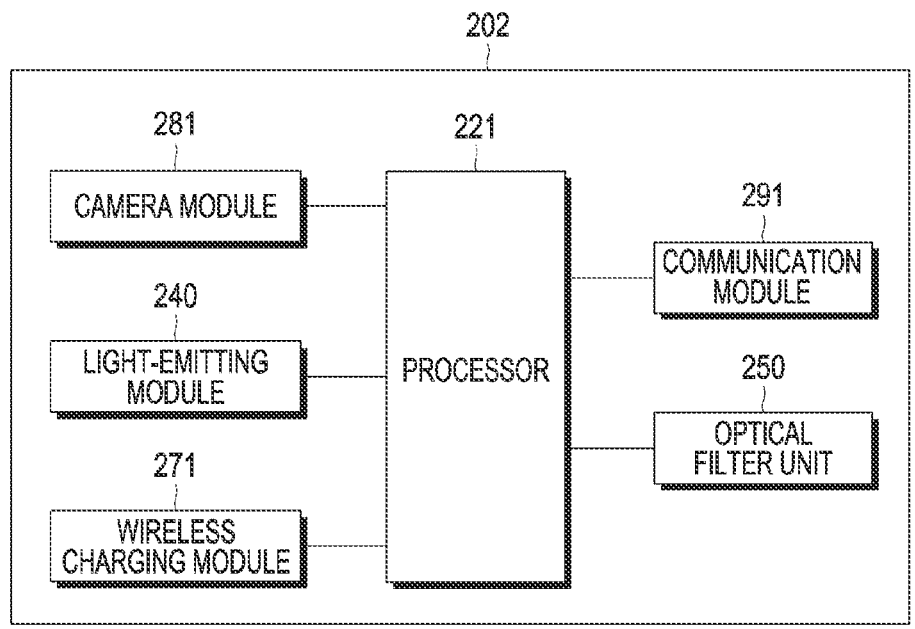
FIG. 3B is a block diagram regarding illustrating an example second electronic device according to various embodiments.

FIG. 3A is a block diagram illustrating an example first electronic device and a server according to various embodiments. FIG. 3B is a schematic block diagram regarding a second electronic device according to various embodiments.

Referring to FIG. 3A, the first electronic device 201 may include a processor (e.g., including processing circuitry) 220, a memory 230, a display 260, a wireless charging module (e.g., including wireless charging circuitry) 270, a camera module (e.g., including a camera) 280, and a communication module (e.g., including communication circuitry) 290.

According to various embodiments, the processor 220 may include various processing circuitry and control overall operations of the first electronic device 201. The processor 220 may be implemented identically or similarly to the processor 120 in FIG. 1.

According to various embodiments, the processor 220 may identify a request for measuring the user's skin condition in a state in which the first electronic device is cradled on the second electronic device. For example, the processor 220 may identify an input for executing an application for measuring the skin condition as the request. For example, the processor 220 may execute an application for measuring the skin condition in response to a request for measuring the skin condition (for example, an input regarding the icon of the corresponding application).

Hereinafter, at least one of operations related to skin measurement performed by the first electronic device 201 or the processor 220 may be controlled by an application. However, it will be assumed herein, for convenience of description, that the operations controlled by the application are performed by the first electronic device 201 or the processor 220, but the disclosure is not limited thereto.

According to various embodiments, the processor 220 may acquire control information for controlling the output of the light-emitting module 240, based on information of the camera module 280 (for example, camera performance information) and information regarding the light-emitting module 240 included in the second electronic device 202. For example, the control information may be information for controlling the output of the light-emitting module 240. The control information may include a parameter value regarding the output intensity of the light-emitting module 240 or the output time point thereof.

According to various embodiments, the processor 220 may control the output of the light-emitting module 240 of the second electronic device 202, based on the control information. While the light-emitting module 240 controlled by the control information outputs light, the processor 220 may acquire at least one image including at least a part of the user's body (for example, the user's face) through the camera module 280.

According to various embodiments, the processor 220 may control the polarizing filter of the second electronic device 202, based on filter control information. The processor 220 may change the direction of polarization of the polarizing filter of the second electronic device 202 using the filter control information, in order to acquire an image corresponding to cross polarization or parallel polarization. For example, the filter control information may refer to information for controlling the direction of polarization of the polarizing filter.

According to various embodiments, the processor 220 may provide information regarding the user's skin condition, based on at least one image. For example, the processor 220 may transmit at least one image to the server 208 and may receive information regarding the skin condition, based on the result of analyzing the at least one image, from the server 208. The processor 220 may provide information regarding the skin condition received from the server 208. The processor 220 may independently analyze the at least one image and may provide information regarding the user's skin condition, based on the result of analysis.

According to various embodiments, the memory 230 may store information regarding the first electronic device 201.

For example, the memory 230 may be implemented identically or similarly to the memory 130 in FIG. 1. For example, the memory 230 may store an image including at least a part of the user's body (for example, face) captured to measure the user's skin condition. In addition, the memory 230 may store information regarding the user's skin condition.

According to various embodiments, the display 260 may display information regarding the first electronic device 201. For example, the display 260 may be implemented identically or similarly to the display device 160 in FIG. 1. For example, the display 260 may display information regarding the user's skin condition. The display 260 may be implemented as a touch screen. The first electronic device 201 may then receive the user's input through the touch screen.

According to various embodiments, the wireless charging module 270 may include various wireless charging circuitry and wirelessly receive power from an external electronic device (for example, second electronic device 202). For example, if the first electronic device 201 is cradled on the cradle 265, the wireless charging module 270 may receive power from the second electronic device 202. For example, the wireless charging module 270 may transmit power in a magnetic resonance type and/or a magnetic induction type.

The camera module 280 may include at least one camera and capture an image including at least a part of the user's body (for example, the user's face). For example, the camera module 280 may include at least one camera.

The communication module 290 may include various communication circuitry and transmit/receive data to/from an external electronic device (for example, server 208 and/or second electronic device 202). The communication module 290 may be implemented identically or similarly to the communication interface 190 in FIG. 1. For example, the first electronic device 201 may transmit a captured image to the server 208 via the communication module 209. In addition, the first electronic device 201 may receive the result of analyzing the image, for example, information regarding the user's skin condition, from the server 208 via the communication module 290.

According to various embodiments, the server 208 may include a processor (e.g., including processing circuitry) 222, a database 235, and a communication module (e.g., including communication circuitry) 292. The server 208 may be implemented identically or similarly to the server 108 in FIG. 1.

According to various embodiments, the processor 222 may include various processing circuitry and control overall operations of the server 208. The processor 222 may be implemented identically or similarly to the processor 120 in FIG. 1. For example, the processor 222 may receive at least one image from the first electronic device 101. The processor 222 may analyze the at least one image and may acquire information regarding the user's skin condition, based on the result of analysis.

According to various embodiments, the processor 222 may transmit the information regarding the user's skin condition to the first electronic device 201 via the communication module 292. In addition, the processor 222 may store the information regarding the user's skin condition in the database 235. For example, the processor 222 may manage and store information regarding the skin condition in the database 235 with regard to each user.

Referring to FIG. 3B, the second electronic device 202 may include a processor (e.g., including processing circuitry) 221, a light-emitting module (e.g., including light-emitting circuitry and/or light-emitting elements) 240, an optical filter unit (e.g., including an optical filter) 250, a wireless charging module (e.g., including wireless charging circuitry) 271, a camera module (e.g., including a camera) 281, and a communication module (e.g., including communication circuitry) 291.

According to various embodiments, the processor 221 may include various processing circuitry and control overall operations of the second electronic device 202. The processor 221 may be implemented identically or similarly to the processor 120 in FIG. 1.

According to various embodiments, the processor 221 may control the light-emitting module 240, based on control information received from the first electronic device 201. In addition, the processor 221 may control the optical filter portion 250, based on filter control information.

According to various embodiments, if the first electronic device 201 is cradled on a cradle 265, the processor 221 may cause the driving of the light-emitting module 240 to stand by. For example, upon identifying that the first electronic device 201 is cradled on the cradle 265, the processor 221 may cause the light-emitting module 240 to enter a standby state in which the same can instantly output light. For example, the processor 221 may identify, using a sensor (for example, a proximity sensor and/or a magnetic sensor), that the first electronic device 201 is cradled on the cradle 265.

According to various embodiments, the processor 221 may receive control information for controlling the light-emitting module 240 from the first electronic device 201. The processor 221 may control the output of light from the light-emitting module, based on the control information.

According to various embodiments, the processor 221 may receive completion information which indicates completion of the image capturing from the first electronic device 201. The processor 221 may stop the output of light from the light-emitting module 240, in response to the completion information.

According to various embodiments, the light-emitting module 240 may include various light-emitting circuitry and/or light-emitting elements and output light for measuring the user's skin condition. The light-emitting module 240 may include at least one light-emitting element. The at least one light-emitting element may output different kinds of light.

According to various embodiments, the optical filter unit 250 may include a polarizing filter and a driving unit capable of moving or rotating the polarizing filter. For example, the optical filter unit 250 may change at least one of the position and the direction of the polarizing filter under the control of the processor 221. For example, the optical filter unit 250 may rotate the direction of polarization of the polarizing filter each time an image is captured. For example, the optical filter unit 250 may rotate the polarizing filter such that the direction of polarization is changed from the vertical direction (or horizontal direction) to the horizontal direction (or vertical direction) each time an image is captured.

According to various embodiments, the wireless charging module 271 may include various wireless charging circuitry and wirelessly transmit power to an external electronic device (for example, first electronic device 201). For example, if the first electronic device 201 is cradled on the cradle 265, the wireless charging module 271 may transmit power to the first electronic device 201.

According to various embodiments, the camera module 281 may include at least one camera and capture an image. For example, upon identifying a request for measuring the user's skin condition, the processor 221 may capture an image including the user's face, while outputting light from the light-emitting module 240. The image captured by the camera module 281 may be stored in the second electronic device 202 or transmitted to another electronic device (for example, first electronic device 201). Alternatively, the image captured by the camera module 281 may be used by the second electronic device 202 to independently measure the user's skin condition.

According to various embodiments, the communication module 291 may include various communication circuitry and transmit/receive data to/from an external electronic device (for example, first electronic device 201 and/or server 208). For example, the second electronic device 202 may transmit the captured image to the first electronic device 201 and/or the server 208 via the communication module 291.

The second electronic device 202 may further include a memory (not illustrated). The memory may store information regarding the second electronic device 202. For example, the memory may store an image including at least a part of the user's body (for example, face), which has been captured to measure the user's skin condition. In addition, the memory may store information regarding the user's skin condition.

Figure 4:
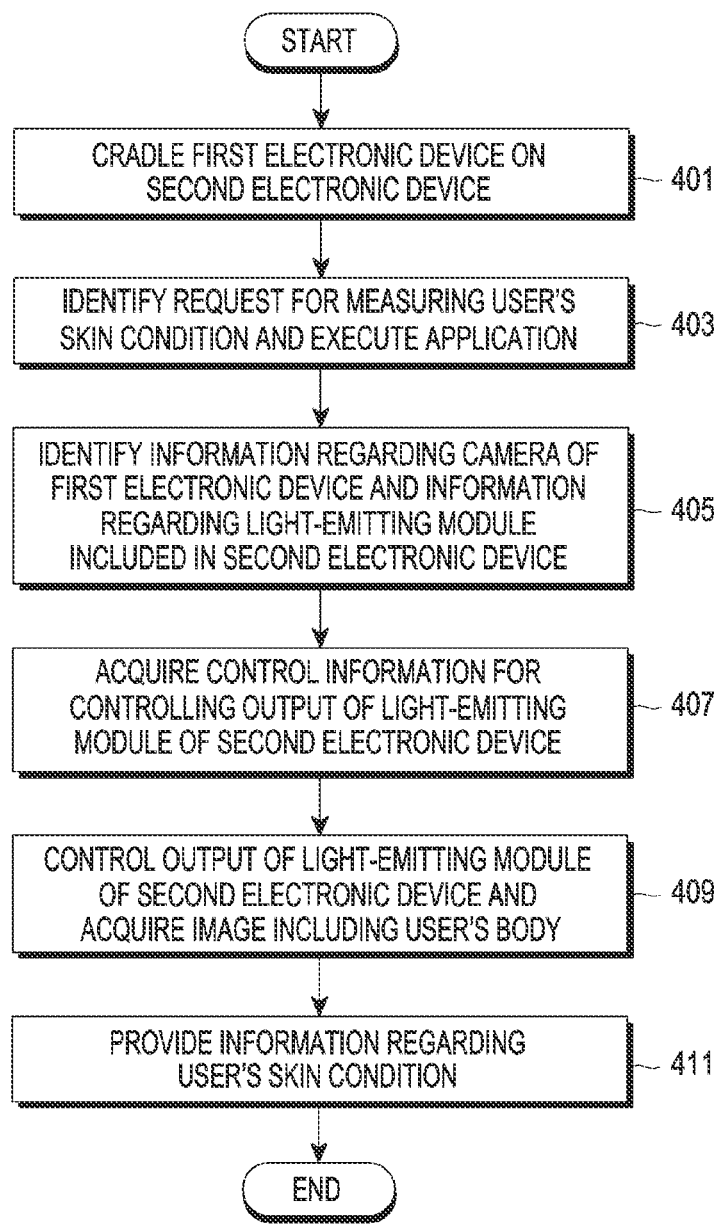
FIG. 4 is a flowchart illustrating example operations of a first electronic device according to various embodiments.

FIG. 4 is a flowchart illustrating example operations of a first electronic device according to various embodiments.

Referring to FIG. 4, according to various embodiments, in operation 401, the first electronic device 201 may be cradled on a second electronic device 202. For example, the first electronic device 201 may be cradled on a cradle (for example, cradle 265 in FIG. 2) of the second electronic device 202.

According to various embodiments, in operation 403, the first electronic device 201 may identify a request for measuring the user's skin condition. In operation 403 first electronic device 201 may also execute an application for measuring the user's skin condition if the request is identified. For example, the request for measuring the user's skin condition may be an input for requesting execution of the application for measuring the user's skin condition.

According to various embodiments, in operation 405, the first electronic device 201 may identify information of a camera (or camera module) included in the first electronic device 201. For example, the information of the camera may include information regarding the performance of the camera (or image sensors included in the camera), for example, at least one of the pixels of the image sensors, the size, the number, the position, the aperture value, the shutter speed, and the sensitivity thereof. In operation 405 first electronic device 201 may further identify information regarding light-emitting modules included in the second electronic device. For example, the information regarding light-emitting modules may include information regarding at least one of the type, the position, the brightness, the output intensity, the size, and the number of the light-emitting modules.

According to various embodiments, in operation 407, the first electronic device 201 may acquire control information for controlling the output of the light-emitting modules of the second electronic device 202. For example, the first electronic device 201 may determine the control information, based on information regarding the camera and information regarding the light-emitting modules. For example, the first electronic device 201 may determine a light-emitting module necessary to capture a specific image, based on the performance of the camera and the position and the type of the light-emitting modules. In addition, the first electronic device 201 may determine the degree of brightness of light to be output by the light-emitting modules, based on the performance of the camera and the position and the output intensity of the light-emitting modules.

According to various embodiments, in operation 409, the first electronic device 201 may control the output of the light-emitting modules of the second electronic device 202. For example, the first electronic device 201 may control the output of a light-emitting module 240 such that, when an image including the user's body is captured through a camera module 280, a level of illuminance optimized to measure the user's skin condition is maintained. In addition, in operation 409, the first electronic device 201 may acquire an image including the user's body, while the output of the light-emitting module is maintained. The first electronic device 201 may change the output of the light-emitting module each time an image is captured. For example, the first electronic device 201 may control the second electronic device 202 so as to output ultraviolet light when an image is captured, and may control the second electronic device 202 so as to output white light when another image is captured.

According to various embodiments, in operation 411, the first electronic device 201 may provide information regarding the user's skin condition, using the acquired image. For example, the first electronic device 201 may display information regarding the user's skin condition on a display (for example, display 260 in FIG. 2).

Figure 5:
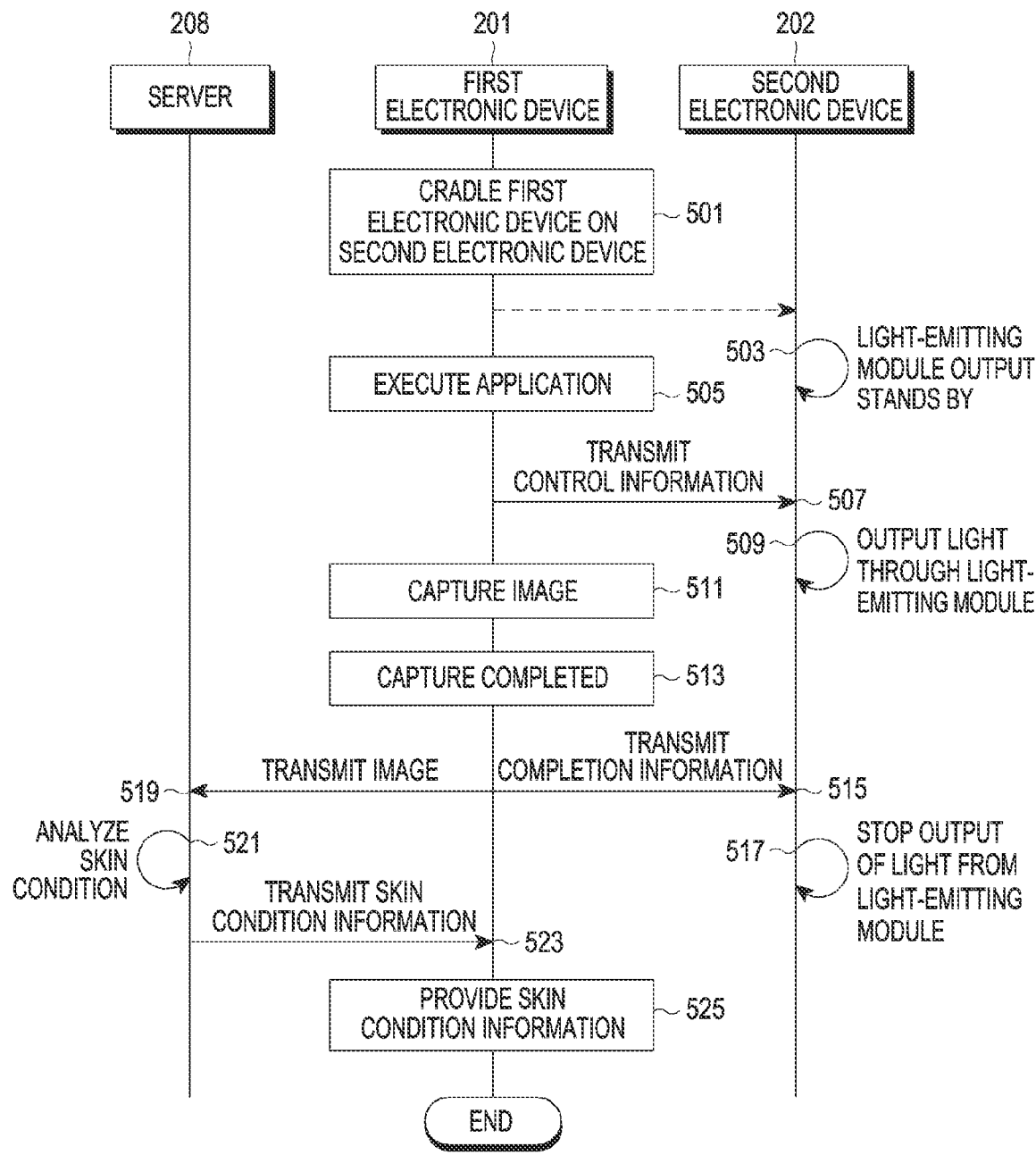
FIG. 5 is a signal flow diagram illustrating example operations of a first electronic device, a second electronic device, and a server according to various embodiments.

FIG. 5 is a signal flow diagram illustrating example operations of a first electronic device, a second electronic device, and a server according to various embodiments.

Referring to FIG. 5, according to various embodiments, in operation 501, the first electronic device 201 may be cradled on the second electronic device 202.

According to various embodiments, in operation 503, the second electronic device 202 may cause the output of a light-emitting module 240 to stand by, upon sensing that the first electronic device 201 is cradled on the second electronic device 202. The output standby state may refer to a state in which an additional command is awaited. For example, the second electronic device 202 may identify whether or not the first electronic device 201 is cradled, using a sensor (for example, a proximity sensor or a pressure sensor) near a cradle 265.

According to various embodiments, the first electronic device 201 may transmit a notification signal via a communication module 290, if the same is cradled on the second electronic device 202. For example, the notification signal may be a signal indicating that the first electronic device 201 has been cradled. The second electronic device 202 may cause the output of the light-emitting module 240 to stand by, in response to receiving the notification signal.

According to various embodiments, in operation 505, the first electronic device 201 may execute an application for measuring the user's skin condition, in response to the user's input. For example, the user's input may be an input for executing an application related to measurement of the skin condition (for example, a touch input regarding the icon of the corresponding application).

According to various embodiments, in operation 507, the first electronic device 201 may transmit control information to the second electronic device 202, in order to control the output of the light-emitting module 240 of the second electronic device 202. For example, the control information may include a command for controlling the output of light from the light-emitting module 240 of the second electronic device 202. The control information may be produced based on information regarding the camera module 280 of the first electronic device 201 (for example, performance of the camera) and information regarding the light-emitting module 240 of the second electronic device 202 (for example, the type, position, and the like of the light-emitting module).

The first electronic device 201 may acquire information regarding the light-emitting module 240 from the second electronic device 202, before producing the control information. The first electronic device 201 may acquire information regarding the light-emitting module 240 from another external device (for example, server 208), before producing the control information.

According to various embodiments, in operation 509, the second electronic device 202 may output light through the light-emitting module 240, based on the control information received from the first electronic device 201. The second electronic device 202 may determine from which of multiple light-emitting modules light is to be output, based on the control information. In addition, the second electronic device 202 may determine in what order the multiple light-emitting modules are to output light, based on the control information. In addition, the second electronic device 202 may determine the intensity of light (or brightness of light) output from at least one of the multiple light-emitting modules, the output time point, and/or the output time, based on the control information.

According to various embodiments, in operation 511, the first electronic device 201 may capture an image for measuring the user's skin condition, while light is output through the light-emitting module 240 of the second electronic device 202. The first electronic device 201 may successively capture multiple images. The first electronic device 201 may successively capture multiple images while changing the light output through the light-emitting module 240. For example, each of the successively acquired images may be acquired in a state in which different kinds of light (for example, ultraviolet/unpolarized white light or cross-polarized light/parallel-polarized light) or light at different levels of brightness is output. For example, the first electronic device 201 may acquire a first image while outputting unpolarized white light through the light-emitting module 240, and may then acquire a second image while outputting ultraviolet rays through the light-emitting module 240. Meanwhile, the first electronic device 201 may display a guide screen regarding image capturing through the display 260. For example, the guide screen may refer to a screen for guiding the user's face to be positioned in a specific area.

According to various embodiments, in operation 513, the first electronic device 201 may finish (complete) image capturing, after acquiring an image sufficient to measure the user's skin condition. In operation 515, the first electronic device 201 may transmit completion information to the second electronic device 202, after the image capturing is completed. In operation 517, the second electronic device 202 may stop the output of light from the light-emitting module 240, in response to receiving the completion information. For example, the completion information may include a control command for stopping the output of light from the light-emitting module 240. The second electronic device 202 may cause the output of the light-emitting module 240 to stand by, after stopping the output of light.

According to various embodiments, in operation 519, the first electronic device 201 may transmit the captured image to the server 208. The first electronic device 201 may transmit, together with the image, information regarding the camera module 280 of the first electronic device 201 (for example, performance information). This may enable the server 208 to analyze and correct the image in view of the performance of the camera module 280.

According to various embodiments, in operation 521, the server 208 may analyze the image. For example, the server 208 may analyze the user's skin condition included in the image, and may acquire information regarding the user's skin condition, based on the result of analysis. In connection with analyzing the user's skin condition, the server 208 may analyze the image in view of the performance of the camera module 280. For example, if the image sensor included in the camera module 280 can acquire a relatively bright image, the server 208 may analyze the skin condition after correcting the brightness of the image. In addition, if the image sensor included in the camera module 280 can acquire a relatively low-quality image, the server 208 may analyze the skin condition after correcting the quality of the image. In addition, the server 208 may store information regarding the skin condition in a database 235.

According to various embodiments, in operation 523, the server 208 may transmit information regarding the skin condition to the first electronic device 201. In operation 525, the first electronic device 201 may provide the information regarding the skin condition. For example, the first electronic device 201 may display the information regarding the skin condition on the display 260. The first electronic device 201 may output the information regarding the skin condition through a speaker (for example, 155 in FIG. 1). In addition, the first electronic device 201 may store the information regarding the skin condition in the memory 230.

Figure 6:
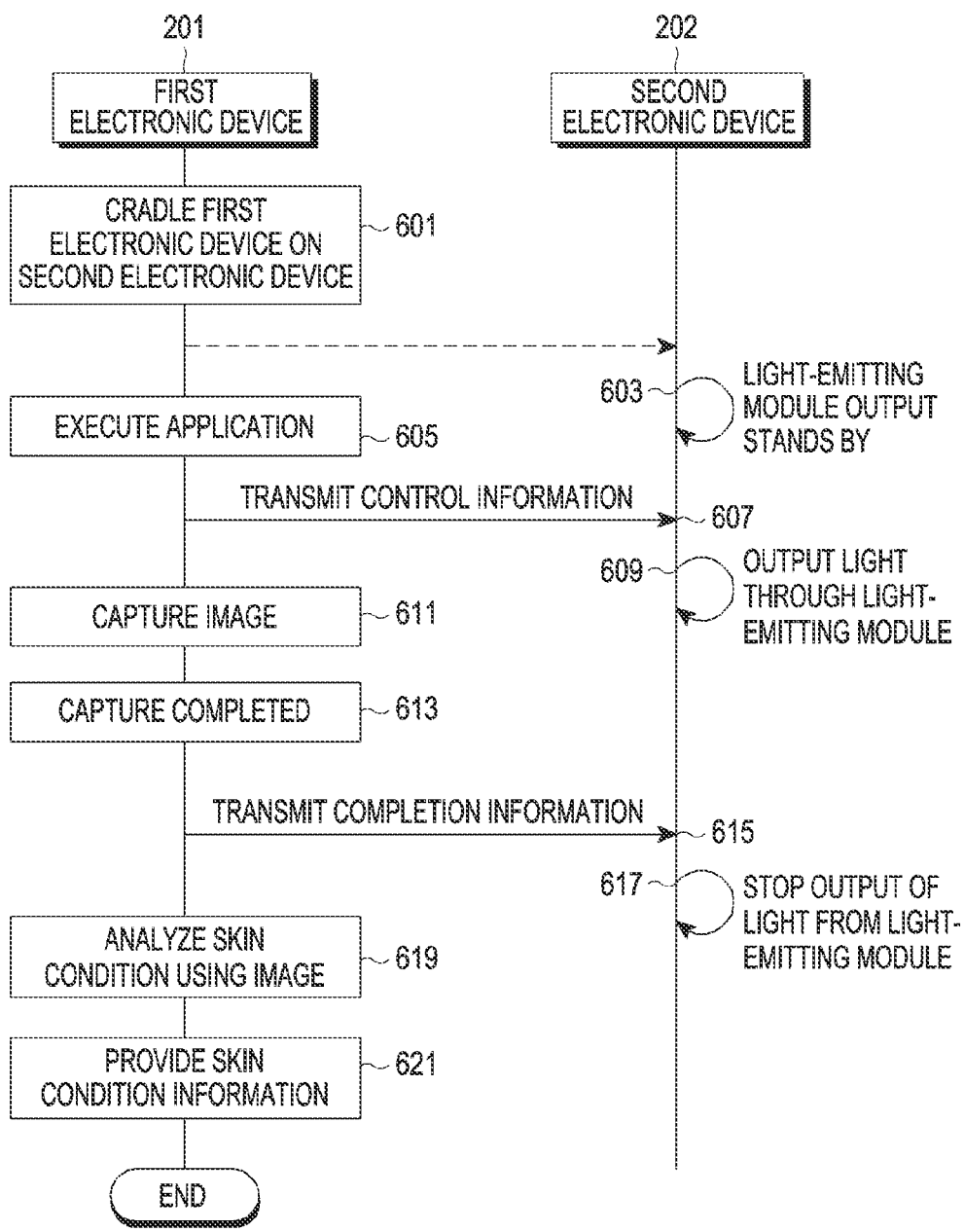
FIG. 6 is a signal flow diagram illustrating example operations of a first electronic device and a second electronic device according to various embodiments.

FIG. 6 is a signal flow diagram illustrating example operations of a first electronic device and a second electronic device according to various embodiments.

Referring to FIG. 6, a comparison of operations of the first electronic device 201 in FIG. 6 with those in FIG. 5 shows that the image analysis operation may be performed by the first electronic device 201, not by the server. According to various embodiments, operation 601 to operation 617 may be implemented identically or similarly to operation 501 to operation 517 in FIG. 5.

According to various embodiments, in operation 619, the first electronic device 201 may identify the user's skin condition by analyzing a captured image. For example, the first electronic device 201 may analyze the user's skin condition included in the image, and may acquire information regarding the user's skin condition, based on the result of analysis. In connection with analyzing the user's skin condition, the first electronic device 201 may analyze the image in view of the performance of the camera module 280. For example, if the camera of the first electronic device 201 can acquire a relatively bright image, the first electronic device 201 may analyze the skin condition after correcting the brightness of the image. In addition, if the camera of the first electronic device 201 can acquire a relatively low-quality image, the first electronic device 201 may analyze the skin condition after correcting the quality of the image.

According to various embodiments, in operation 621, the first electronic device 201 may provide information regarding the skin condition. For example, the first electronic device 201 may display the information regarding the skin condition on the display 260. The first electronic device 201 may output the information regarding the skin condition through a speaker (for example, 155 in FIG. 1). In addition, the first electronic device 201 may store the information regarding the skin condition in the memory 230.

Figure 7:
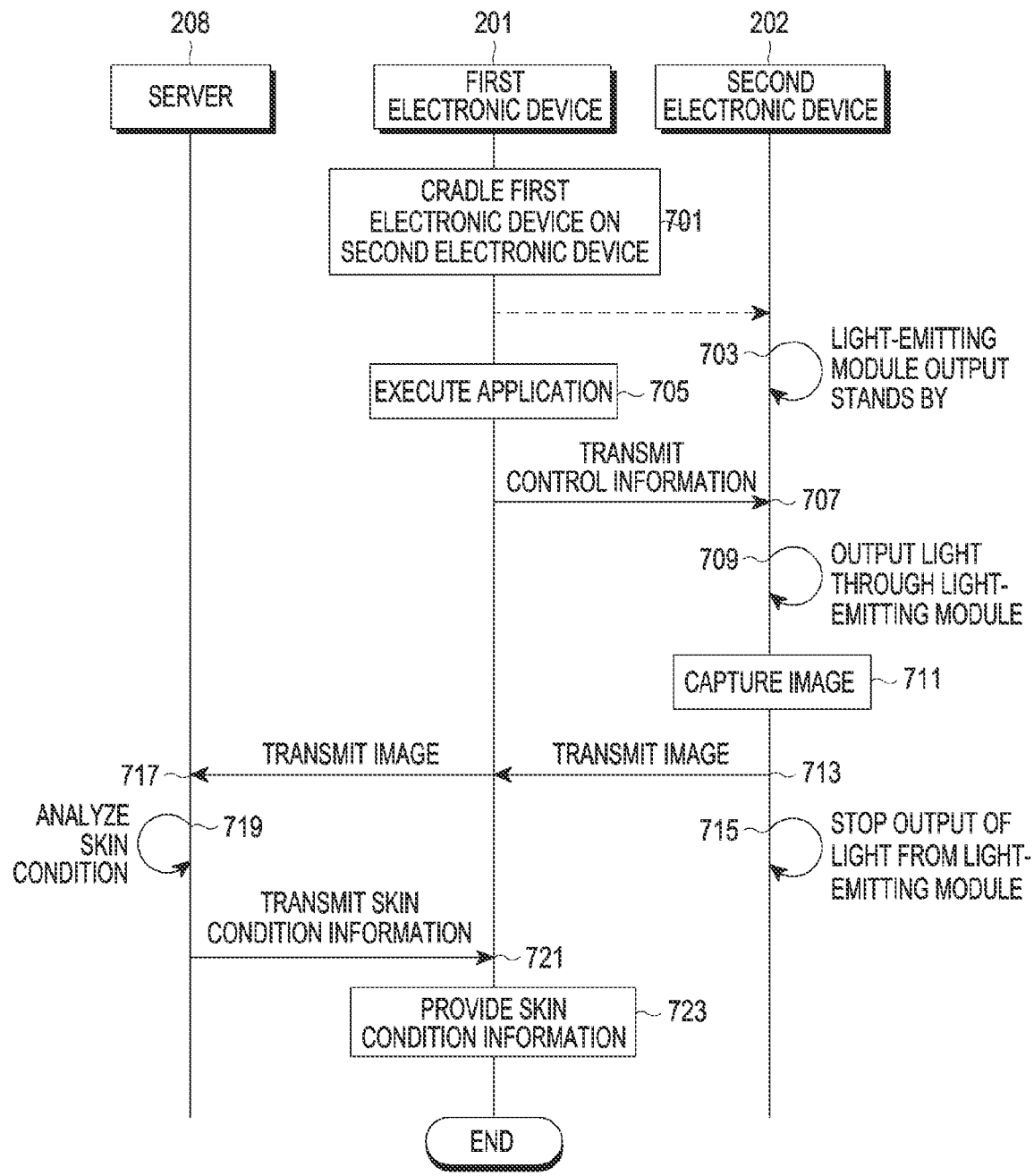
FIG. 7 is a signal flow diagram illustrating example operations of a first electronic device, a second electronic device, and a server according to various embodiments.

FIG. 7 is a signal flow diagram illustrating example operations of a first electronic device, a second electronic device, and a server according to various embodiments.

Referring to FIG. 7, a comparison of operations in FIG. 7 with those in FIG. 5 and FIG. 6 shows that the image analysis operation may be performed by the second electronic device 202, not by the first electronic device 201. According to various embodiments, operation 701 to operation 705 may be implemented identically or similarly to operation 501 to operation 505 in FIG. 5.

According to various embodiments, in operation 707, the first electronic device 201 may transmit control information for controlling the output of the light-emitting module 240 and image capturing to the second electronic device 202. The control information may include a command for controlling the output of light from the light-emitting module 240 and for capturing an image through the camera module 280.

According to various embodiments, in operation 709, the second electronic device 202 may output light through the light-emitting module 240 and may capture an image through the camera module 281, based on the control information.

According to various embodiments, in operation 711, the second electronic device 202 may capture an image for measuring the user's skin condition using the camera module 281, while light is output through the light-emitting module 240. The first electronic device 201 may display a guide screen regarding image capturing through the display 260. The second electronic device 202 may successively capture multiple images. The second electronic device 202 may successively capture multiple images while changing the light output through the light-emitting module 240. For example, each of the successively acquired images may be acquired in a state in which different kinds of light (for example, ultraviolet/unpolarized white light or cross-polarized light/parallel-polarized light) or light at different levels of brightness is output.

According to various embodiments, in operation 713, after the capturing is completed, the second electronic device 202 may transmit the captured image to the first electronic device 201. According to another embodiment, the second electronic device 202 may transmit the captured image to the server 208. The second electronic device 202 may transmit, together with the image, information regarding the camera module 281 of the second electronic device 202 (for example, performance information) to the first electronic device 201 or the server 208. In operation 715, after the capturing is completed, the second electronic device 202 may stop the output of light from the light-emitting module 240. The second electronic device 202 may cause the output of the light-emitting module 240 to stand by, until an additional control command is received.

According to various embodiments, in operation 717, the first electronic device 201 may transmit the captured image to the server 208. The first electronic device 201 may transmit, together with the image, information regarding the camera module 281 of the second electronic device 202 (for example, performance information). This enables the server 208 to analyze and correct the image in view of the performance of the camera module 281.

According to various embodiments, in operation 719, the server 208 may analyze the image. For example, the server 208 may analyze the user's skin condition included in the image, and may acquire information regarding the user's skin condition, based on the result of analysis. In connection with analyzing the user's skin condition, the server 208 may analyze the image in view of the performance of the camera module 281. For example, if the camera of the second electronic device 202 can acquire a relatively bright image, the server 208 may analyze the skin condition after correcting the brightness of the image. In addition, if the camera of the second electronic device 202 can acquire a relatively low-quality image, the server 208 may analyze the skin condition after correcting the quality of the image. In addition, the server 208 may store information regarding the skin condition in a database 235.

According to various embodiments, in operation 721, the server 208 may transmit information regarding the skin condition to the first electronic device 201. In operation 723, the first electronic device 201 may provide the information regarding the skin condition. For example, the first electronic device 201 may display the information regarding the skin condition on the display 260. The first electronic device 201 may output the information regarding the skin condition through a speaker (for example, 155 in FIG. 1). In addition, the first electronic device 201 may store the information regarding the skin condition in the memory 230.

According to various embodiments, the second electronic device 202 may acquire an image for measuring the user's skin condition regardless of whether or not the first electronic device 201 is cradled, may analyze the image, and may provide information regarding the skin condition. For example, the second electronic device 202 may acquire an image of the user while independently outputting light through the light-emitting module 240, and may analyze the acquired image. In addition, the second electronic device 202 may acquire and store information regarding the user's skin condition, based on the result of analysis. The information regarding the skin condition may be transmitted to the first electronic device 201.

Figure 8:
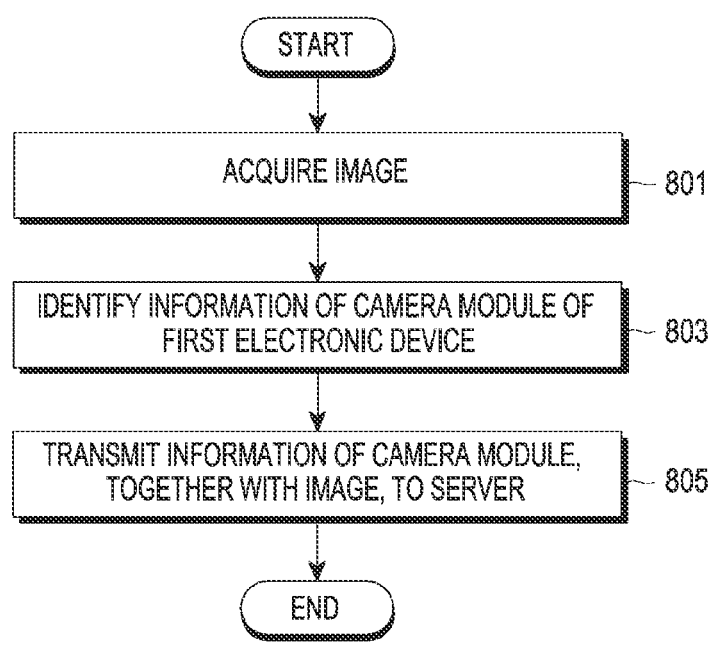
FIG. 8 is a flowchart illustrating example operations of a first electronic device transmitting an image to a server, according to various embodiments.

FIG. 8 is a flowchart illustrating example operations of a first electronic device transmitting an image to a server, according to various embodiments.

Referring to FIG. 8, in operation 801, the first electronic device (for example, first electronic device 201 in FIG. 2) may acquire an image using a camera module (for example, camera module 280 in FIG. 2), while light is output from a light-emitting module 240 of a second electronic device (for example, second electronic device 202 in FIG. 2).

According to various embodiments, in operation 803, the first electronic device 201 may identify information of the camera module 280 of the first electronic device 201. For example, the information of the camera module 280 may be information regarding the performance of the camera module 280, for example, information regarding the performance of an image sensor included in the camera module 280. The first electronic device 201 may acquire information regarding the camera module 280 from a memory 230 or may acquire information regarding the camera module 280 from an external server.

According to various embodiments, in operation 805, the first electronic device 201 may transmit, together with the acquired image, information of the camera module 280 to a server 208. When the server 208 has already acquired information regarding the camera module 280, the first electronic device 201 may transmit only an image to the server 208. For example, when the server 208 has previously acquired information regarding the camera module 280 from the first electronic device 201, the first electronic device 201 may transmit only an image to the server 208.

Figure 9:
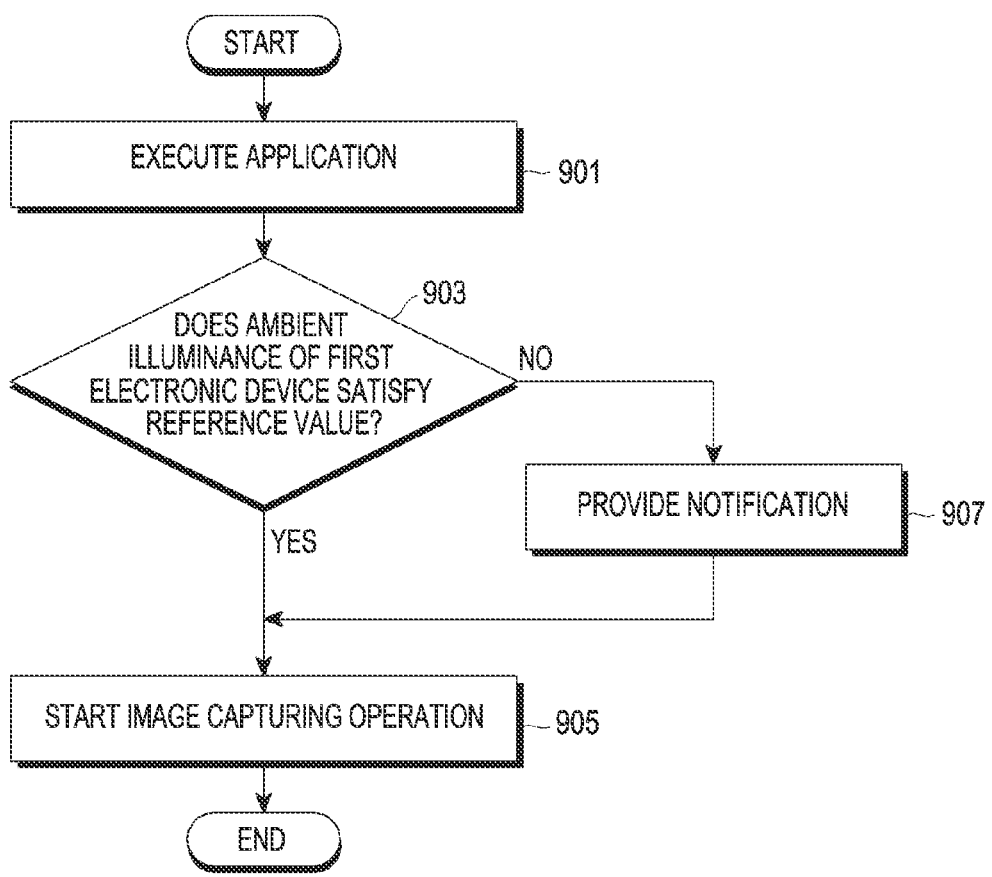
FIG. 9 is a flowchart illustrating example operations of a first electronic device identifying ambient illuminance according to various embodiments.

FIG. 9 is a flowchart illustrating example operations of a first electronic device identifying ambient illuminance according to various embodiments.

Referring to FIG. 9, in operation 901, the first electronic device 201 may execute an application for measuring the user's skin condition, after being cradled on a second electronic device 202. For example, the first electronic device 201 may execute an application for measuring the user's skin condition, in response to the user's request, for example, an input regarding the icon of the corresponding application.

According to various embodiments, in operation 903, the first electronic device 201 may identify the ambient illuminance of the first electronic device 201 and may identify whether the ambient illuminance satisfies a reference value. For example, the first electronic device 201 may identify the ambient illuminance using an illuminance sensor (for example, 176 in FIG. 1) included in the first electronic device 201. The first electronic device 201 may receive information regarding the ambient illuminance from the second electronic device 202. For example, the first electronic device 201 may receive an illuminance value sensed by an illuminance sensor (for example, 176 in FIG. 1) of the second electronic device 202 through a communication module 290, and may identify the ambient illuminance, based on the received illuminance value. The reference value may refer to an illuminance value or a range of illuminance values, which is appropriate for capturing an image for measuring the user's skin condition. The reference value may be automatically configured by a processor 220 in advance, or may be manually configured by the user. For example, if the ambient illuminance is too bright or too dark, the ambient illuminance may not satisfy the reference value. For example, in the case of image capturing requiring ultraviolet light that may be used to measure a UV spot on skin or porphyrin, the first electronic device 201 may configure the image capturing operation so as to begin only when the ambient illuminance is equal to/lower than a specific reference value (for example, 10 lux).

According to various embodiments, if the ambient illuminance satisfies the reference value (Yes in operation 903), the first electronic device 201 may, in operation 905, start an image capturing operation. For example, the image capturing operation may include operations of controlling the light-emitting module of the second electronic device 202 and capturing an image.

According to various embodiments, if the ambient illuminance does not satisfy the reference value (No in operation 903), the first electronic device 201 may, in operation 907, provide a visual, tactile, and/or auditory notification. For example, the first electronic device 201 may display a notification, on the display 260, indicating the ambient illuminance is to be adjusted. In addition, if the first electronic device 201 can control ambient lighting devices, the first electronic device 201 may control the ambient lighting devices such that the ambient illuminance satisfies the reference value. In addition, if the ambient illuminance does not satisfy the reference value, the first electronic device 201 may perform no image capturing operation.

Figure 10:
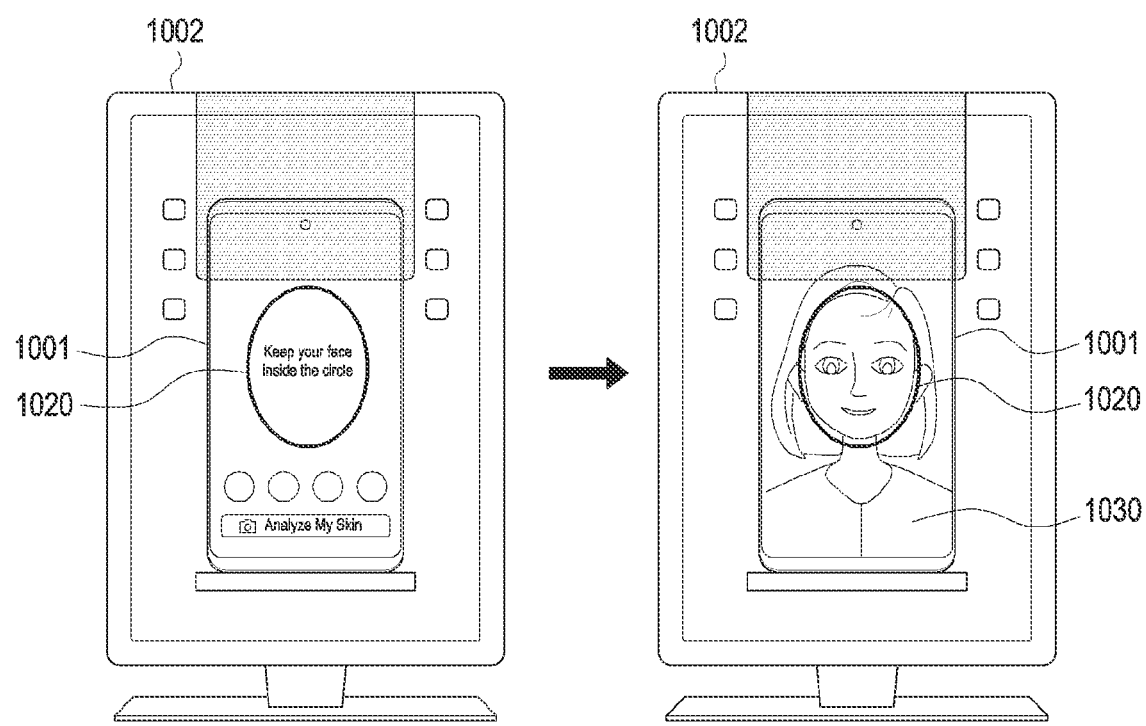
FIG. 10 is a diagram illustrating an example operation of a first electronic device providing a guide screen according to various embodiments.

FIG. 10 is a diagram illustrating an example operation of a first electronic device providing a guide screen according to various embodiments.

Referring to FIG. 10, the first electronic device 1001 (for example, first electronic device 201 in FIG. 2) may be cradled on a second electronic device 1002 (for example, second electronic device 202 in FIG. 2).

Figure 11:
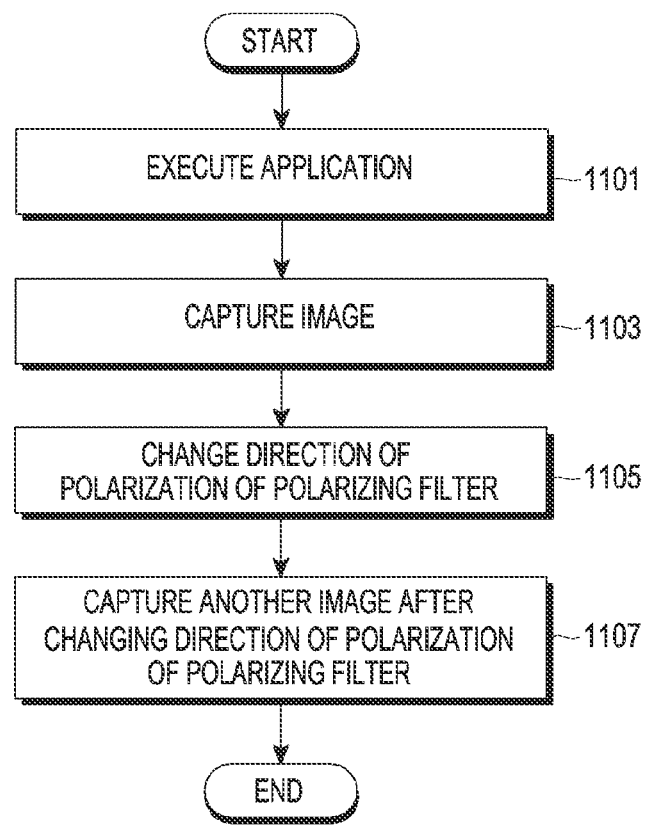
FIG. 11 is a flowchart illustrating an example operation of a first electronic device controlling a polarizing filter of a second electronic device according to various embodiments.

According to various embodiments, if an application for measuring the skin condition is executed, the first electronic device 1001 may display a guide screen 1020 on a display. For example, the guide screen 1020 may refer to a screen for guiding the user's face to be positioned in a specific area such that skin measurement can be performed normally. For example, the guide screen may include a screen for designating an area corresponding to the user's face. For example, solid lines or dotted lines may be used to designate the area, and a quadrangular or circular area may be designated. The user 1030 may efficiently position his/her face inside the guide screen 1020 using the guide screen 1020. FIG. 11 is a flowchart illustrating an example operation of a first electronic device controlling a polarizing filter of a second electronic device.

Referring to FIG. 11, according to various embodiments, in operation 1101, the first electronic device 201 may execute an application for measuring the user's skin.

According to various embodiments, in operation 1103, the first electronic device 201 may perform an image capturing operation.

According to various embodiments, in operation 1105, the first electronic device 201 may change the direction of polarization of the polarizing filter included in (or attached to) the second electronic device 202, each time at least one image is captured. The first electronic device 201 may transmit filter control information for changing the direction of polarization of the polarizing filter of the second electronic device 202. The second electronic device 202 may change the direction of polarization in response to the filter control information. For example, the polarizing filter may include a polarizing filter covering the camera of the first electronic device 201 and/or a polarizing filter covering at least a part of the light-emitting module thereof. For example, the first electronic device 201 may change the direction of polarization by rotating the polarizing filter.

According to various embodiments, in operation 1107, the first electronic device 201 may capture another image after changing the direction of polarization of the polarizing filter. The first electronic device 201 may thereby acquire a cross-polarized image and a parallel-polarized image. For example, the cross-polarized image may be obtained by suppressing light directly reflected at the skin surface. The parallel-polarized image may be obtained by reinforcing light directly reflected at the skin surface. The first electronic device 201 may use at least one of the cross-polarized image and the parallel-polarized image according to the item of analysis of the skin to be measured (or the type of skin analysis). For example, the first electronic device 201 may use the cross-polarized image when measuring skin pigmentation or other trouble. The first electronic device 201 may use the parallel-polarized image when measuring a microstructure such as small wrinkles on the skin.

Figure 12A:
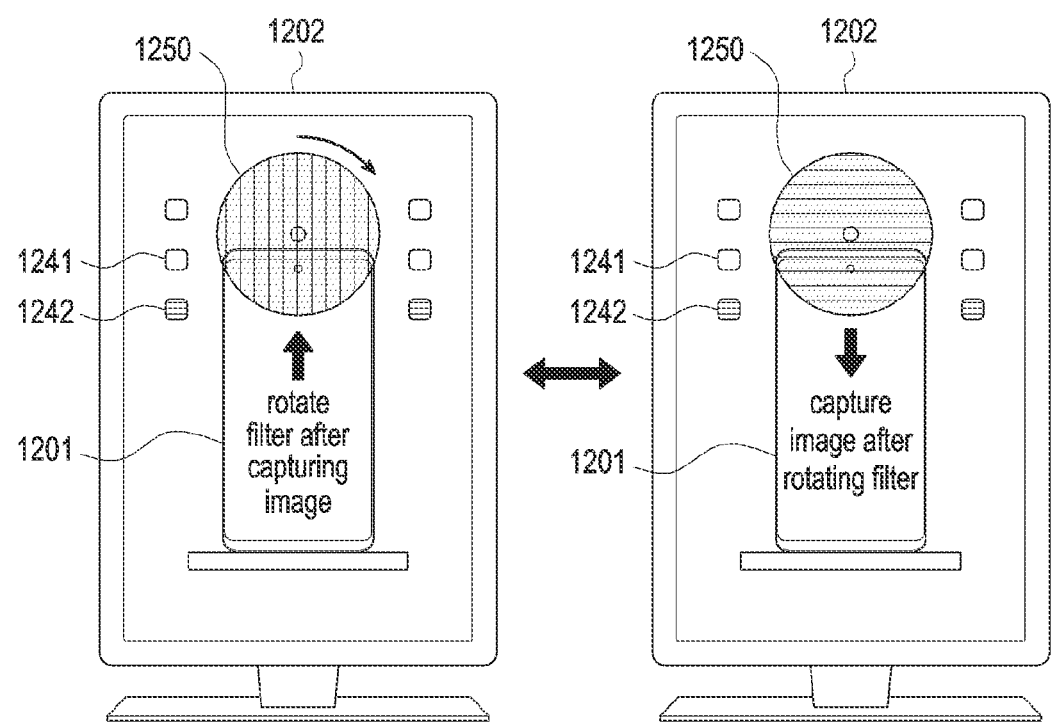
FIG. 12A is a diagram illustrating an example operation of a first electronic device controlling a polarizing filter of a second electronic device according to various embodiments.
Figure 12B:
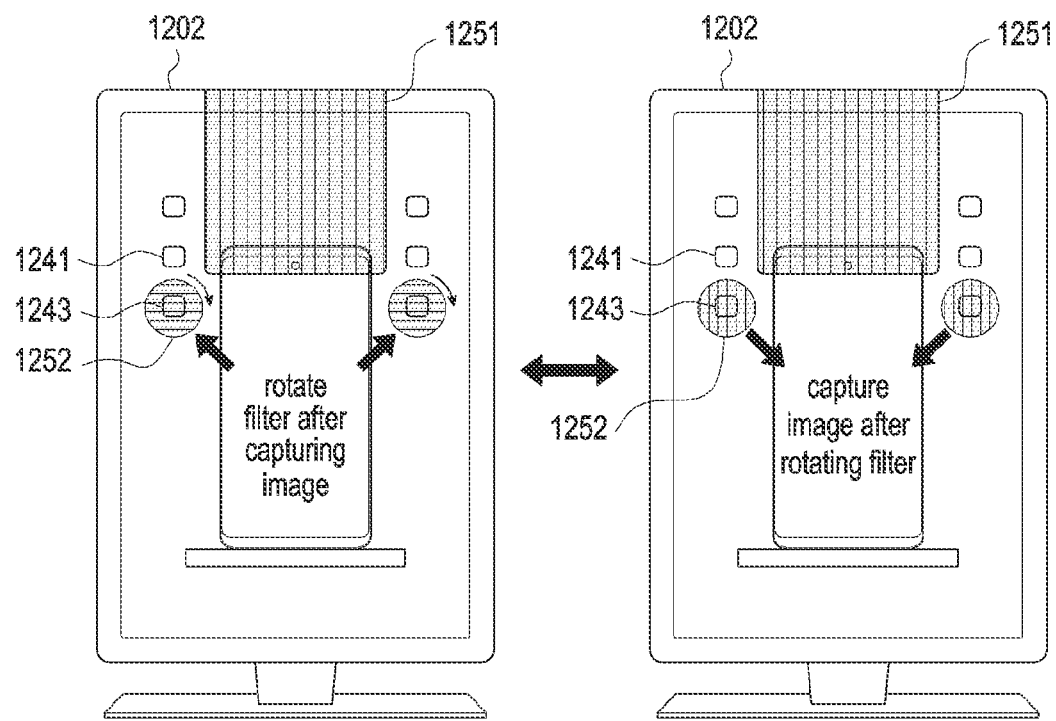
FIG. 12B is a diagram illustrating an example operation of a first electronic device controlling a polarizing filter of a second electronic device according to various embodiments.

FIG. 12A is a diagram illustrating an example operation of a first electronic device controlling a polarizing filter of a second electronic device according to various embodiments, and FIG. 12B is a diagram illustrating an example operation of a first electronic device controlling a polarizing filter of a second electronic device according to various embodiments.

Referring to FIG. 12A and FIG. 12B, the first electronic device 1201 (for example, first electronic device 201 in FIG. 2) may be cradled on the second electronic device 1202 (for example, second electronic device 202 in FIG. 2). FIG. 12A and FIG. 12B may illustrate methods for acquiring a cross-polarized image and a parallel-polarized image in various types. For example, the cross-polarized image may be produced based on polarized rays intersecting in different directions. The parallel-polarized image may be produced based on polarized rays in parallel with each other.

Referring to FIG. 12A, the second electronic device 1202 may include an unpolarized light-emitting element 1241, a polarized light-emitting element 1242, and a polarizing filter 1250. For example, the polarized light-emitting element 1242 may output only a polarized component in a specific direction (for example, horizontal polarizing direction). The polarizing filter 1250 may transmit a polarized component in a specific direction (for example, vertical or horizontal polarizing direction).

According to various embodiments, the second electronic device 1202 may output light from the unpolarized light-emitting element 1241 or the polarized light-emitting element 1242 under the control of the first electronic device 1201.

According to various embodiments, the first electronic device 1201 may capture a cross-polarized image using the polarizing filter 1250 in the vertical polarizing direction in a state in which light has been output from the polarized light-emitting element 1242. After capturing the cross-polarized image, the first electronic device 1201 may control the second electronic device 1202 such that the polarizing filter 1250 rotates by, for example, 90°. After the polarizing filter 1250 rotates by 90°, the first electronic device 1201 may capture a parallel-polarized image using the polarizing filter 1250 in the horizontal polarizing direction in a state in which light has been output from the polarized light-emitting element 1242.

According to various embodiments, the first electronic device 1201 may capture an unpolarized image without using the polarizing filter 1250 (for example, after detaching the polarizing filter 1250) in a state in which light has been output from the unpolarized light-emitting element 1241.

According to various embodiments, the first electronic device 1201 may capture an image similar to the unpolarized image without using the polarizing filter 1250 in a state in which light has been output from the unpolarized light-emitting element 1241. That is, when only one of the polarizing element and the camera has a polarizing filter positioned thereon, the first electronic device 1201 may capture an image similar to the unpolarized image using normal unpolarized white light, without a large effect such as the cross polarization or parallel polarization.

Referring to FIG. 12B, the second electronic device 1202 may include a first unpolarized light-emitting element 1241, a second unpolarized light-emitting element 1243, a first polarizing filter 1251, and a second polarizing filter 1252. For example, the second unpolarized light-emitting element 1423 may be covered by the second polarizing filter 1252 capable of transmitting only a polarized component in a specific direction (for example, vertical or horizontal polarizing direction). The second polarizing filter 1252 may, depending on the position, transmit a polarized component in the vertical or horizontal polarizing direction. For example, a state in which the second polarizing filter 1252 transmits a polarized component in the horizontal polarizing direction may be assumed as a first state, and a state in which the same transmits a polarized component in the vertical polarizing direction may be assumed as a second state. For example, the first polarizing filter 1251 may be configured to transmit only a polarized component in the vertical polarizing direction.

According to various embodiments, the second electronic device 1202 may output light from the first unpolarized light-emitting element 1241 or the second unpolarized light-emitting element 1243 under the control of the first electronic device 1201.

According to various embodiments, if light is output from the second unpolarized light-emitting element 1243 while the second polarizing filter 1252 is in the first state, the first electronic device 1201 may capture a cross-polarized image using the first polarizing filter 1251. After capturing the cross-polarized image, the first electronic device 1201 may control the second electronic device 1202 such that the second polarizing filter 1252 rotates by 90°. If light is output from the second unpolarized light-emitting element 1243 while the second polarizing filter 1252 is in the first state in which the same is rotated by 90°, the first electronic device 1201 may capture a parallel-polarized image using the first polarizing filter 1251.

According to various embodiments, the first electronic device 1201 may capture an unpolarized image without using the first polarizing filter 1251 (for example, after the first polarizing filter 1251 is detached) in a state in which light has been output from the first unpolarized light-emitting element 1241.

According to various embodiments, the first electronic device 1201 may capture (or acquire) an unpolarized image, a cross-polarized image, and/or a parallel-polarized image according to the characteristics of the skin condition to be measured.

Figure 13A:
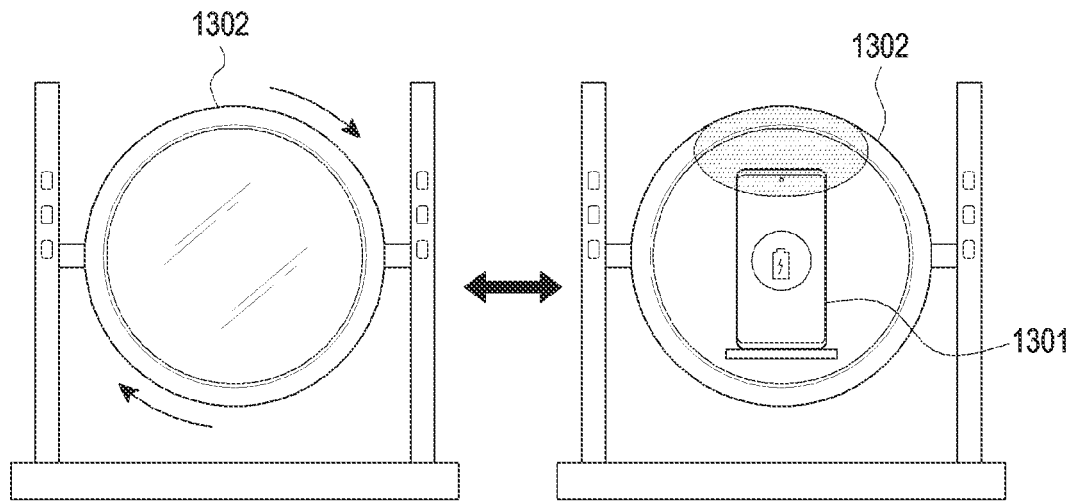
FIG. 13A is a diagram illustrating an example first electronic device and a second electronic device according to various embodiments.
Figure 13B:
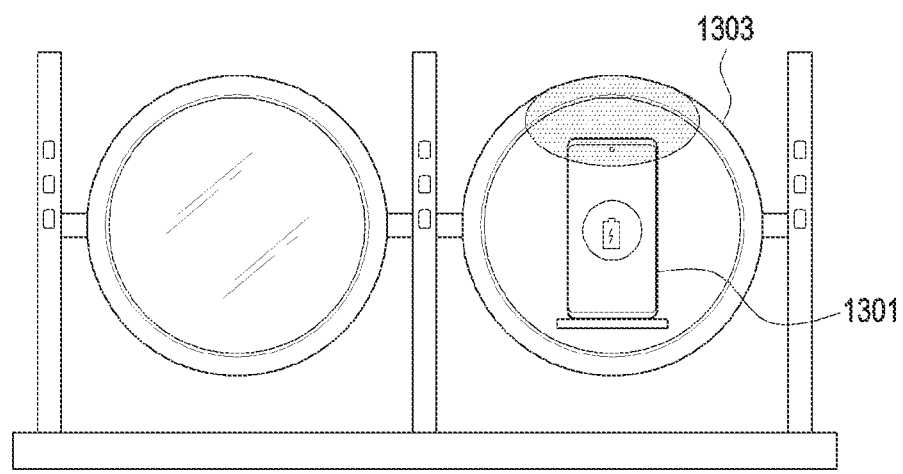
FIG. 13B is a diagram illustrating an example first electronic device and a second electronic device according to various embodiments.

FIG. 13A is a diagram illustrating an example first electronic device and a second electronic device according to various embodiments, and FIG. 13B is a diagram illustrating an example first electronic device and a second electronic device according to various embodiments.

Referring to FIG. 13A, according to various embodiments, the first electronic device 1301 may be cradled on the second electronic device 1302. For example, if the second electronic device 1302 is a rotating smart mirror, the first electronic device 1301 may be cradled on the rear part of the mirror positioned on the front portion thereof. After being cradled on the second electronic device 1302, the first electronic device 1301 may wirelessly receive power from the second electronic device 1302. For example, the user may use the mirror on the front portion of the second electronic device 1302 in normal occasions and, when measuring the skin, may cradle the first electronic device 1301 on the rear portion of the second electronic device 1302, thereby measuring the skin condition.

According to various embodiments, the second electronic device 1302 may include supports on both sides of the mirror. A light-emitting module may be disposed on the supports of the electronic device 1302. Alternatively, the light-emitting module may be disposed on the rear part of the mirror of the electronic device 1302.

Referring to FIG. 13B, according to various embodiments, the first electronic device 1301 may be cradled on the second electronic device 1303. For example, unlike the case in FIG. 13A, the second electronic device 1303 may have a separate cradle next to the mirror, not on the front/rear portion thereof, such that the first electronic device 1301 is cradled thereon. For example, the user may use the mirror on the left part of the second electronic device 1303, and may cradle the first electronic device 1301 on the right part of the second electronic device 1303, thereby measuring the skin condition.

FIG. 14A is a diagram illustrating a result of measuring the user's skin according to the brightness of light output from a light-emitting module of a second electronic device, and FIG. 14B is a diagram illustrating a result of measuring the user's skin according to the brightness of light output from a light-emitting module of a second electronic device.

Referring to FIG. 14A, the first electronic device (for example, first electronic device 201 in FIG. 2) may acquire a first image under a condition having an insufficient amount of light. For example, the first image may be acquired using indoor lighting only. The first image may poorly reproduce the actual skin condition. The first electronic device 201 may fail to provide accurate information regarding the skin condition, based on the first image.

Referring to FIG. 14B, the first electronic device 201 may acquire a second image under a condition having a sufficient amount of light. For example, the second image may be acquired using light output from the light-emitting module 240 of the second electronic device 202 (for example, second electronic device 202 in FIG. 2). The second image may reproduce the actual skin condition with a high degree of accuracy. The first electronic device 201 may provide more accurate information regarding the skin condition, based on the second image.

On the other hand, if an image acquired under a condition having an excessive amount of light is used, the first electronic device 201 may fail to provide accurate information regarding the skin condition. This is because the corresponding image may poorly reproduce the actual skin condition. Therefore, the first electronic device 201 may control the light-emitting module of the second electronic device 202 so as to provide a sufficient amount of light when capturing images.

FIG. 15A is a diagram illustrating a result of measuring the user's skin using a polarizing filter of a second electronic device according to various embodiments, FIG. 15B is a diagram illustrating a result of measuring the user's skin using a polarizing filter of a second electronic device according to various embodiments, and FIG. 15C is a diagram illustrating a result of measuring the user's skin using a polarizing filter of a second electronic device according to various embodiments.

Referring to FIG. 15A, the first electronic device 201 (for example, first electronic device in FIG. 2) may acquire an unpolarized first image. For example, the first image may be acquired using no separate polarizing filter.

Referring to FIG. 15B, the first electronic device 201 may acquire a cross-polarized second image. For example, the second image may be acquired while the polarizing direction of a polarizing filter that covers a camera intersects with the polarizing direction of a polarizing filter that covers a light-emitting element. The second image may be produced while suppressing light directly reflected at the skin surface, compared with the first image. The first electronic device 201 may use the second image to analyze pigmentation or other skin troubles, which is mainly used to measure the inside of the skin.

Referring to FIG. 15C, the first electronic device 201 may acquire a parallel-polarized third image. For example, the third image may be acquired while the polarizing direction of a polarizing filter that covers a camera is identical to the polarizing direction of a polarizing filter that covers a light-emitting element. The third image may be produced while enhancing light directly reflected at the skin surface, compared with the first image. The first electronic device 201 may use the third image to analyze small wrinkles and the like, which is mainly used to measure microstructures of skin.

Therefore, the first electronic device 201 may control the optical filter according to the characteristics of the skin condition to be measured.

A first electronic device according to various example embodiments may include: a display; a communication module comprising communication circuitry; a camera module including at least one camera; and a processor. The processor may be configured to: identify a request for measuring a skin condition of a user in a state in which the first electronic device is cradled on a second electronic device; acquire, based on information of the camera module and information regarding at least one light-emitting element included in the second electronic device, control information for controlling output of light from the at least one light-emitting element; control output of light from the at least one light-emitting element of the second electronic device based on the control information; acquire at least one image including at least a part of a body of the user through the camera module while light is output through the at least one light-emitting element controlled by the control information; and provide information regarding the skin condition of the user using the at least one image.

The processor may be configured to: transmit the at least one image to a server through the communication module; and acquire information regarding the skin condition from the server through the communication module.

The processor may be configured to transmit information regarding the first electronic device to the server together with the at least one image.

The processor may be configured to acquire information regarding the at least one light-emitting element from the second electronic device.

The information regarding the at least one light-emitting element may include information regarding at least one of the type, the position, the output intensity, the size, and the number of the at least one light-emitting element.

The information regarding the camera module may include information regarding at least one of pixels, the size, the number, the position, the aperture value, the shutter speed, and the sensitivity of image sensors included in the camera module.

The processor may be configured to execute an application for measuring the skin condition in response to receiving the request for measuring the skin condition of the user.

The processor may be configured to display a guide screen for capturing an image of the user's face through the display before acquiring the at least one image.

The processor may be configured to: identify filter control information for controlling at least one polarizing filter included in the second electronic device; and control the at least one polarizing filter, based on the filter control information.

The processor may be configured to change the polarizing direction of the at least one polarizing filter based on each of the at least one image being acquired.

The second electronic device may be implemented as a smart mirror.

A method for operating a first electronic device according to various example embodiments may include: identifying a request for measuring a skin condition of a user in a state in which the first electronic device is cradled on a second electronic device; acquiring, based on information of a camera included in the first electronic device and information regarding at least one light-emitting element included in the second electronic device, control information for controlling output of light from the at least one light-emitting element; controlling output of light from the at least one light-emitting element of the second electronic device based on the control information; acquiring at least one image including at least a part of a body of the user through the camera while light is output through the at least one light-emitting element controlled by the control information; and providing information regarding the skin condition of the user using the at least one image.

The providing information regarding the skin condition may include transmitting the at least one image to a server; and acquiring information regarding the skin condition from the server.

The transmitting the at least one image to the server may include transmitting information regarding the first electronic device to the server together with the at least one image.

The method for operating a first electronic device may further include: identifying filter control information for controlling at least one polarizing filter included in the second electronic device; and controlling the at least one polarizing filter, based on the filter control information.

The controlling the at least one polarizing filter may include changing the polarizing direction of the at least one polarizing filter when each of the at least one image is acquired.

An electronic device according to various example embodiments may include: at least one light-emitting element; and a processor. The processor may be configured to: control the at least one light-emitting element to enter a standby state based on an external electronic device being cradled on the electronic device; control the at least one light-emitting element to output light based on control information acquired from the external electronic device, the control information being determined based on information of a camera module of the external electronic device and information regarding the at least one light-emitting element; and stop output of light from the at least one light-emitting element based on image capturing by the external electronic device being completed.

The electronic device may further include at least one polarizing filter, and the processor may be configured to change the direction of the at least one polarizing filter based on filter control information acquired from the external electronic device.

The electronic device may further include a camera module including at least one camera, and the processor may be configured to: acquire at least one image including the user's face while controlling output of light from the at least one light-emitting element based on a request for measuring the user's skin condition being identified; and control communication circuitry to transmit the at least one image to the external electronic device.

The electronic device may include a smart mirror.

Each of the elements described in various embodiments of the disclosure may include one or more components, and the names of the corresponding elements may vary depending on the type of electronic device. In various embodiments, the electronic device may include at least one of the elements disclosed herein. Some of the elements may be omitted from or other additional elements may be further included in the electronic device. Also, some of the elements of the electronic device according to various embodiments may be combined into one entity, which may perform functions identical to those of the relevant elements before the combination.

While the disclosure has been illustrated and described with reference to various example embodiments, it will be understood that the various example embodiments are intended to be illustrative, not limiting. It will be further understood by one of ordinary skill in the art that various changes in form and detail may be made without departing from the true spirit and full scope of the disclosure, including the appended claims and their equivalents.

What is claimed is:

1. A first electronic device comprising:
a display;
a communication module comprising communication circuitry;
a camera module including at least one camera; and
a processor, wherein
the processor is configured to:
identify a request for measuring a skin condition of a user in a state in which the first electronic device is cradled on a second electronic device;
acquire information regarding the at least one light-emitting element from the second electronic device;
generate, based on information of the camera module and the information regarding at least one light-emitting element included in the second electronic device, control information for controlling output of the at least one light-emitting element;
control output of the at least one light-emitting element of the second electronic device based on the control information;
control the camera module to successively capture a plurality of images while changing kind and/or level of brightness of light output through the at least one light-emitting element controlled based on the control information;
acquire the plurality of images comprising at least a part of a body of the user through the camera module, wherein the plurality of images are acquired in a state in which different kinds of light and/or light at different levels of brightness is output; and
provide information regarding the skin condition of the user using at least one image of the plurality of images,
wherein the control information includes at least one parameter value of output intensity of the light, an output timepoint or an output time, and
wherein the processor is configured to, when controlling the output of the at least one light-emitting element:
identify the at least one parameter value of the at least one light-emitting element based on the information of the camera module and the information regarding at least one light-emitting element,
set a control command for changing the output of the light of the at least one light-emitting element based the at least one parameter value, and
control the communication module to transmit the control information including the control command to the second electronic device.

2. The first electronic device of claim 1, wherein the processor is configured to:
control the communication module to transmit the at least one image to a server; and
acquire information regarding the skin condition from the server through the communication module.

3. The first electronic device of claim 2, wherein the processor is configured to control the communication module to transmit information regarding the first electronic device to the server together with the at least one image.

4. The first electronic device of claim 1, wherein the information regarding the at least one light-emitting element comprises information regarding at least one of a type, position, output intensity, size, and number of the at least one light-emitting element.

5. The first electronic device of claim 1, wherein the information regarding the camera module comprises information regarding at least one of pixels, size, number, position, aperture value, shutter speed, and sensitivity of image sensors included in the camera module.

6. The first electronic device of claim 1, wherein the processor is configured to execute an application for measuring the skin condition in response to receiving a request for measuring the skin condition of the user.

7. The first electronic device of claim 1, wherein the processor is configured to control the display to display a guide screen for capturing an image of the user's face before acquiring the at least one image.

8. The first electronic device of claim 1, wherein the processor is configured to:
identify filter control information for controlling at least one polarizing filter included in the second electronic device; and
control the at least one polarizing filter based on the filter control information.

9. The first electronic device of claim 8, wherein the processor is configured to change a polarizing direction of the at least one polarizing filter based on each of the at least one image being acquired.

10. The first electronic device of claim 1, wherein the second electronic device is implemented as a smart mirror.

11. A method of operating a first electronic device, the method comprising:
identifying a request for measuring a skin condition of a user in a state in which the first electronic device is cradled on a second electronic device;
acquiring information regarding the at least one light-emitting element from the second electronic device;
generating, based on information of a camera included in the first electronic device and the information regarding at least one light-emitting element included in the second electronic device, control information for controlling output of the at least one light-emitting element;
controlling output of the at least one light-emitting element of the second electronic device based on the control information;
controlling a camera module, comprising at least one camera, to successively capture a plurality of images while changing kind and/or level of brightness of light output through the at least one light-emitting element controlled based on the control information;
acquiring the plurality of images comprising at least a part of a body of the user through the camera, wherein the plurality of images are acquired in a state in which different kinds of light and/or light at different levels of brightness is output; and
providing information regarding the skin condition of the user using at least one image of the plurality of images,
wherein the control information includes at least one parameter value of output intensity of the light, an output timepoint or an output time, and
wherein the controlling the output of the at least one light-emitting element of the second electronic device based on the control information comprises:
identifying the at least one parameter value of the at least one light-emitting element based on the information of the camera module and the information regarding at least one light-emitting element;
setting a control command for changing the output of the light of the at least one light-emitting element based the at least one parameter value; and
transmitting the control information including the control command to the second electronic device.

12. The method of claim 11, wherein the providing information regarding the skin condition comprises:
transmitting the at least one image to a server; and
acquiring information regarding the skin condition from the server.

13. The method of claim 12, wherein the transmitting the at least one image to the server comprises transmitting information regarding the first electronic device to the server together with the at least one image.

14. The method of claim 11, further comprising:
identifying filter control information for controlling at least one polarizing filter included in the second electronic device; and
controlling the at least one polarizing filter based on the filter control information.

15. The method of claim 14, wherein the controlling the at least one polarizing filter comprises changing a polarizing direction of the at least one polarizing filter based on each of the at least one image being acquired.

16. A second electronic device comprising:
at least one light-emitting element; and
a processor, wherein
the processor is configured to:
control the at least one light-emitting element to enter a standby state for based on a first electronic device being cradled on the second electronic device;
transmit information regarding the at least one light-emitting element to the first electronic device;
receive control information including a control command from the first electronic device;
control the at least one light-emitting element to output light by changing kind and/or level of brightness of the light based on the control information acquired from the first electronic device, the control information being generated based on information of a camera module of the external electronic device and the information regarding the at least one light-emitting element; and
stop output of light from the at least one light-emitting element based on image capturing by the first electronic device being completed,
wherein the control information includes at least one parameter value of output intensity of the light, an output timepoint or an output time, and
wherein the control command is set, by the first electronic device, to change the output of the light of the at least one light-emitting element based the at least one parameter value.

17. The second electronic device of claim 16, wherein the second electronic device further comprises at least one polarizing filter, and
wherein the processor is configured to change a direction of the at least one polarizing filter based on filter control information acquired from the external electronic device.

18. The second electronic device of claim 16, wherein second the electronic device further comprises a camera module including at least one camera, and
wherein the processor is configured to:
acquire at least one image comprising the user's face while controlling output of light from the at least one light-emitting element based on a request for measuring the user's skin condition being identified; and
transmit the at least one image to the first electronic device.

19. The second electronic device of claim 16, wherein the second electronic device comprises a smart mirror.

* * * * *